(12) United States Patent
Zaidi et al.

(10) Patent No.: US 10,155,120 B2
(45) Date of Patent: Dec. 18, 2018

(54) FAST IDENTIFICATION OF SHOCKABLE OR NON-SHOCKABLE RHYTHMS IN ECG DATA

(71) Applicant: ZOLL Medical Corporation, Chelmsford, MA (US)

(72) Inventors: Naveed Zaidi, Shrewsbury, MA (US); Frederick J. Geheb, Danvers, MA (US); Qing Tan, Somerville, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 9 days.

(21) Appl. No.: 15/405,377

(22) Filed: Jan. 13, 2017

(65) Prior Publication Data

US 2017/0225001 A1    Aug. 10, 2017

Related U.S. Application Data

(60) Provisional application No. 62/279,713, filed on Jan. 16, 2016.

(51) Int. Cl.
| | |
|---|---|
| *A61N 1/00* | (2006.01) |
| *A61N 1/39* | (2006.01) |
| *A61B 5/0402* | (2006.01) |
| *A61N 1/04* | (2006.01) |

(52) U.S. Cl.
CPC .......... *A61N 1/3987* (2013.01); *A61B 5/0402* (2013.01); *A61N 1/0484* (2013.01)

(58) Field of Classification Search
CPC ... A61N 1/3925; A61N 1/3987; A61N 1/3993
USPC .......................................................... 607/5
See application file for complete search history.

(56) References Cited

U.S. PATENT DOCUMENTS

| | | |
|---|---|---|
| 7,565,194 B2 | 7/2009 | Tan et al. |
| 2011/0202101 A1 | 8/2011 | Tan et al. |
| 2013/0282068 A1 | 10/2013 | Sagiroglu et al. |
| 2013/0282072 A1 | 10/2013 | Abdeen et al. |

(Continued)

FOREIGN PATENT DOCUMENTS

WO    WO 2014/141080    9/2014

OTHER PUBLICATIONS

"Rhythm Analysis during Cardiopulmonary Resuscitation: Past, Present, and Future" (De Gauna, Sr et al.) BioMed Research International Review Article. Jan. 9 2014; vol. 2014, pp. 1-14. http://dx.dol.org/10.1155/2014/386010, accessed Mar. 30, 2017.

(Continued)

*Primary Examiner* — Amanda Hulbert
*Assistant Examiner* — Philip C Edwards
(74) *Attorney, Agent, or Firm* — Fish & Richardson P.C.

(57) ABSTRACT

Methods and systems that analyze electrocardiogram (ECG) data to identify whether it would be beneficial for a caregiver to administer an electric shock to the heart in an effort to get the heart back into a normal pattern and a consistent, strong beat. By conducting a running check for conditions that are pre-validated by a comprehensive patient database to have high predictive value (e.g., with a low false-positive rate), a shockable rhythm can be identified fast (e.g., less than 6 seconds, less than 3 seconds, possibly in less than a second) and without having to analyze ECG data for longer time segments than would otherwise be required using conventional methods.

32 Claims, 21 Drawing Sheets

(56) References Cited

U.S. PATENT DOCUMENTS

2014/0046394 A1 2/2014 Allavatam et al.
2015/0352369 A1 12/2015 Quan et al.

OTHER PUBLICATIONS

International Search Report and Written Opinion in International Application No. PCT/US17/13310 dated May 16, 2017, 21 pages.

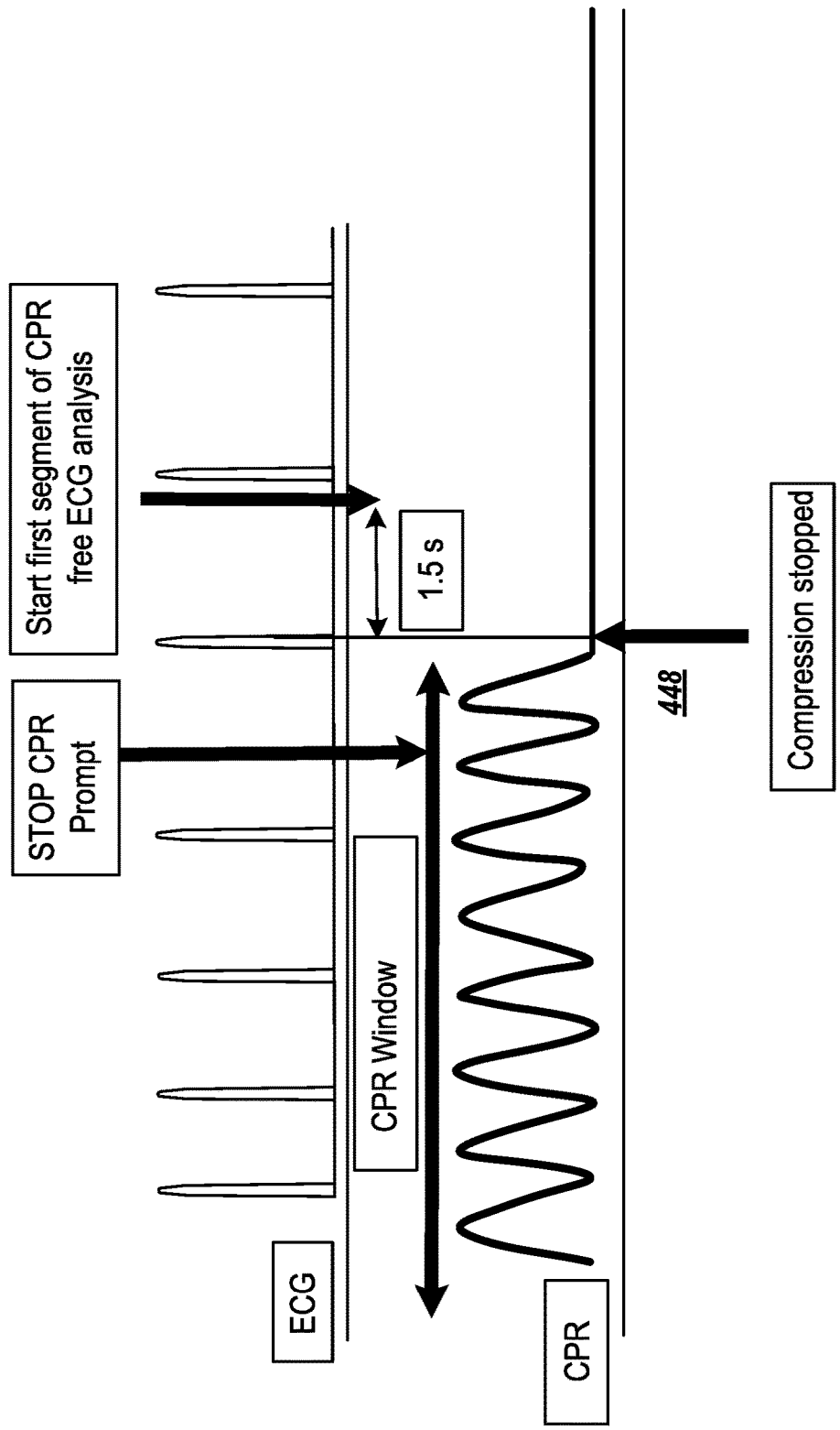

FAST IDENTIFICATION OF SHOCKABLE OR NON-SHOCKABLE RHYTHMS IN ECG DATA

CLAIM OF PRIORITY

This application claims priority under 35 USC § 119(e) to U.S. Patent Application Ser. No. 62/279,713, filed on Jan. 16, 2016, the entire contents of which are hereby incorporated by reference.

TECHNICAL FIELD

This document relates to cardiac resuscitation systems and techniques, in particular, defibrillators that apply defibrillation shocks to a patient's heart through appropriately placed electrodes.

BACKGROUND

Heart attacks are a common cause of death. A heart attack occurs when a portion of the heart tissue loses circulation and becomes damaged as a result (e.g., because of blockage in the heart vasculature). Heart attacks and other abnormalities can lead to ventricular fibrillation (VF), which is an abnormal heart rhythm (arrhythmia) that causes the heart to lose pumping capacity. VF occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life. If such problems are not corrected quickly—typically within minutes—the rest of the body is deprived of oxygen and the person dies. Therefore, prompt care of a person experiencing ventricular fibrillation can be key to a positive outcome for such a person.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns. People who have had previous problems may be implanted with an automatic defibrillator that constantly monitors the condition of their heart and applies a shock when necessary. Other such people may be provided with a wearable defibrillator in the form of a vest such as the ZOLL® LIFEVEST® wearable cardioverter defibrillator product provided by ZOLL Medical Corporation. Other people may be treated using an external defibrillator/monitor, such as those found in a hospital or used by emergency medical services, for example, the R SERIES® or X SERIES® products from ZOLL Medical Corporation. Some people may be treated via an automated external defibrillator (AED) of the kind that is frequently seen in airports, public gymnasiums, schools, shopping areas and other public spaces. Examples of such AEDs are the AED PLUS® automated external defibrillator or the AED PRO® automated external defibrillator, both from ZOLL Medical Corporation of Chelmsford, Mass. As provided herein, the term AED refers generically to any device or system that incorporates some method or algorithm of acquiring an electrocardiographic (ECG) signal, analyzing the ECG for whether or not it is appropriate to provide a defibrillation shock to the patient(s) and which can provide a defibrillation shock.

SUMMARY

The present disclosure provides methods and systems that analyze electrocardiogram (ECG) data to identify whether it would be beneficial for a caregiver to administer an electric shock to the heart in an effort to get the heart back into a normal pattern and a consistent, strong beat. By conducting a running check for conditions that are pre-validated by a comprehensive patient database to have high predictive value (e.g., with a low false-positive rate), a shockable rhythm can be identified fast (e.g., less than 6 seconds, less than 3 seconds, between 0.1-3 seconds, between 0.1-2 seconds, possibly in less than a second, between 0.1-1 second) and without having to analyze ECG data for longer time segments than would otherwise be required using conventional methods. In some implementations, a variable-length time segment of an ECG signal is processed such that one or more features of the time segment is usable in determining, with at least a threshold level of accuracy (e.g., previously validated by the gold standard of patient data to be highly predictive), whether an ECG rhythm provided by a monitored ECG signal of the patient is shockable or non-shockable. For example, the variable-length time segment may involve an initial time period that is incrementally extendable by one or more time periods (e.g., less than or equal to 3 seconds, between 0.1-3 seconds, less than or equal to 2.5 seconds, between 0.1-2.5 seconds, less than or equal to 2 seconds, between 0.1-2 seconds, less than or equal to 1.5 seconds, between 0.1-1.5 seconds, less than or equal to 1 second, between 0.1-1 second, less than or equal to 0.5 seconds, between 0.1-0.5 seconds, etc.) depending on whether more processing of the ECG signal is necessary to make a final determination of whether the ECG signal is producing a rhythm that is shockable or non-shockable.

To reach a decision of whether the ECG signal represents a shockable or non-shockable rhythm as quickly as possible, it may be preferable for the defibrillating system to be vigilant in identifying whether an interruption in CPR chest compressions has occurred. For example, the defibrillating system may employ one or more sensors (e.g., ECG electrode(s), accelerometer(s), motion sensor(s)) for tracking chest compressions, and as soon as the defibrillating system detects a gap or interruption in chest compressions, the system may commence ECG analysis, immediately or shortly thereafter. If the system is unable to come to a conclusion of shockable or non-shockable prior to when chest compressions recommence, the system may continue to detect when the next interruption in chest compressions occurs, so that ECG analysis may readily begin again.

In some implementations, an initial rule set may be applied to the initial time period of the variable-length time segment where various features of the ECG signal within the initial time period are assessed. Such an assessment based on the initial rule set is useful for determining whether the patient is in a shockable or non-shockable state, or whether more time is needed to make a decision. If the variable-length time segment is extended (by an appropriate period of time), then an adjusted rule set may be applied to the adjusted time period, further assessing various features of the ECG signal within the adjusted time period. A determination may then be made based on the adjusted rule set as to whether the patient is in a shockable or non-shockable state, or whether more time is needed to make a decision. This process may be repeated until a decision is made as to whether the patient is in a shockable or non-shockable state.

In some implementations, the technology described in this document may provide one or more of the following advantages.

By providing a running check based on conditions that are pre-validated to have low false positive rates, time needed to identify shockable rhythms in a patient's ECG data may be reduced. Such reductions in identification time can be potentially life-saving for the patient. The resulting early feedback may allow a caregiver more time to reach a decision, and therefore be ready to pursue a particular course of action sooner. For example, if a defibrillator takes five seconds to charge, and a caregiver is notified of the presence of a shockable rhythm within one second of the charging time, the caregiver has four or more seconds to be ready to administer the shock as soon as the charging is complete. Or, if the defibrillator is already charged and a rhythm is determined to be shockable using methods according to the present disclosure, the shock may be immediately administered without further need for analysis or other forms of delay. Pre-validating the conditions using one or more large databases of patient data can help in identifying accurate conditions that may be used with a high degree of confidence.

Other features and advantages will be apparent from the description and drawings, and from the claims.

DESCRIPTION OF DRAWINGS

FIGS. 4G-4L show examples of ECG waveforms in relation to CPR treatments.

Like reference symbols in the various drawings indicate like elements.

DETAILED DESCRIPTION

Figure 1:
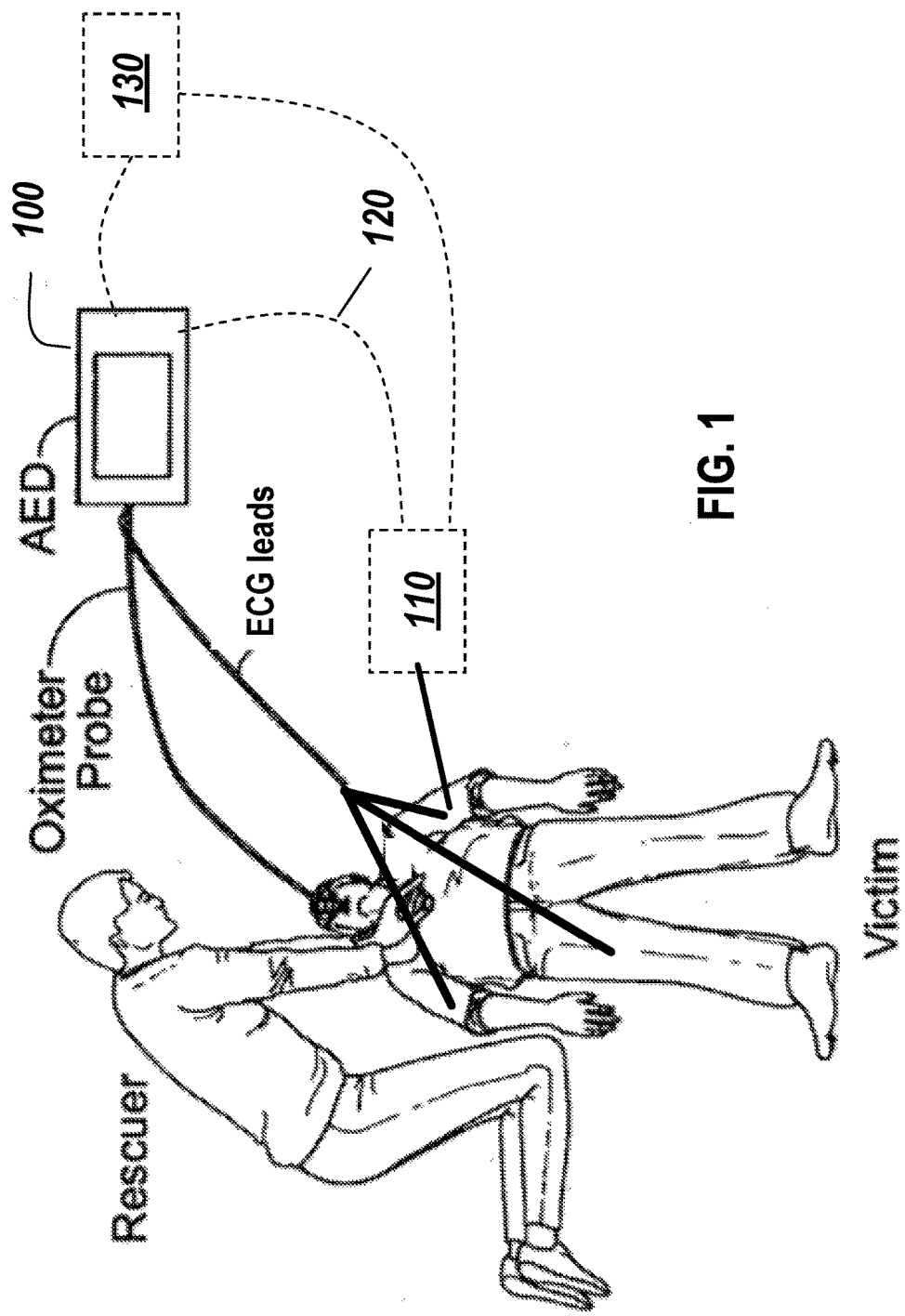
FIG. 1 shows a victim of cardiac arrest being cared for using a medical device.

The present disclosure is directed to methods and systems that analyze electrocardiogram (ECG) data of a patient to provide feedback to a caregiver (e.g., a rescue personnel) and/or medical device(s) (e.g., defibrillators) used to treat the patient on whether an electric shock should be administered to the patient's heart in an effort to get the heartbeat back into a normal pattern. In particular, the present disclosure describes conducting a running check for conditions that are pre-validated to have a high accuracy.

The positive predictive value (PPV) is provided herein as:

PPV=(Number of True Positives)/(Total Number of Negative Determinations)

Where a "true positive" (TP) is an event where the test makes a positive prediction, and the subject has a positive result under the gold standard provided from a comprehensive patient database, and a "false positive" (FP) is an event where the test makes a positive prediction, and the subject has a negative result under the gold standard. In this case, a positive prediction is that the ECG rhythm is shockable. The gold standard is typically the review of the ECG rhythm by two or more qualified independent cardiologists during the algorithm development phase.

The negative predictive value (NPV) is provided herein as:

NPV=(Number of True Negatives)/(Total number of Negative Determinations)

Where a "true negative" (TN) is an event where the test makes a negative prediction, and the subject has a positive result under the gold standard, and a "false negative" (FN) is the event that the test makes a negative prediction, and the subject has a negative result under the gold standard. In this case, a negative prediction is that the ECG rhythm is non-shockable.

As provided herein, a clause is an expression that defines constraints on features of an ECG waveform underlying the ECG data; a clause is said to be met (or satisfied) if the criteria of the clause are met by the features of the ECG waveform being analyzed. In particular, if the criteria are met, then the ECG rhythm is said to be shockable or non-shockable, depending on the particular clause. In the description of this present invention, when we refer to, "clause" alone, we refer generically to both shockable and non-shockable clauses.

In some examples, a particular clause is a high accuracy clause if the clause is applied to a portion of an ECG signal meeting a threshold time length (e.g., a length associated with the particular clause) needed to achieve a certain level of accuracy, for a determination of shockable or non-shockable to be made. Further, the same clause may be a normal accuracy clause if the clause is applied to a portion of an ECG signal that does not meet the threshold time length, e.g., the portion of the ECG signal has a length less than the threshold time length. In this way, as the length of the ECG signal portion increases, accuracy tends to increase as well. Thus, there will be a minimum time segment length below which a clause is only a normal accuracy clause, and is not suitable as a high accuracy clause, but for time segment lengths longer than this minimum length, the clause is then considered to be a high accuracy clause.

It is not always the case that a clause that is sufficiently accurate for one duration will be sufficiently accurate for all durations in excess of the initial clause length. Thus, the clause accuracy needs to be tested against the gold standard database for all duration clauses that the clause rule set is going to be used.

For instance, there may be clauses for which the minimum time segment length for making a determination of whether the ECG rhythm is shockable or non-shockable is 1 second, which are termed "1-second clauses." For instance, there may be clauses for which the minimum time segment length for making the determination is 2 seconds, which are termed "2-second clauses." For instance, there may be clauses for which the minimum time segment length for making the determination is 3 seconds, which are termed "3-second clauses." Depending on how the clauses are tested against the gold standard of the comprehensive database of patient information, the clauses may be categorized according to the associated level of certainty (e.g., accuracy, which may be based on certain combined levels of sensitivity and specificity, or on the PPV and/or NPV) that they provide. For example, clauses that exhibit a high predictive certainty, e.g. accuracy, based on PPV and/or NPV may be categorized as high accuracy clauses, and clauses that exhibit lower predictive certainty may not be categorized as high accuracy clauses. In various implementations, for certain time periods of analysis (e.g., an initial time period), when a high accuracy clause is met, a decision of whether a rhythm represented by an analyzed ECG signal is shockable or non-shockable may be made immediately, without need for further analysis. In contrast, if no high accuracy clauses are encountered, then the time period is extended and the rules are adjusted to create new high-accuracy clauses for the extended time period.

For instance, if no high accuracy clause is met during a particular period of analysis (e.g., the initial time period, such as 1 second, 2 seconds, 3 seconds, etc.), then it may be determined that more time is needed to make a definitive decision of shockable or non-shockable.

In such an example, new or modified rules will be used over the longer time interval to achieve a sufficient level of accuracy. In some cases, the algorithm may submit a vote of shockable or non-shockable over multiple time segments within the extended time period. Accordingly, the initial high accuracy clause(s) may make up an initial rule set which only requires the initial time period (e.g., 0.1, 0.5, 1.0, 1.5, 2.0, 2.5, or 3 seconds). The adjusted rule set requires both the initial time period plus one or more additional time periods (e.g., 0.1, 0.5, 1.0, 1.5, 2.0, 2.5, 3.0 seconds, 6-9 seconds).

Clauses may be developed according to findings provided by the medical community. For example, it is well known that a ventricular fibrillation (VF) rhythm, which involves uncoordinated ventricular muscle quivering that makes the heart unable to pump blood, is shockable. It is also well known that a ventricular tachycardia (VT) rhythm, which involves a rapid heartbeat arising from improper cardiac electrical activity, is also shockable. In contrast, an asystole rhythm, characterized by a flatline where the heart is in a state of no electrical activity, is non-shockable. An ECG signal that shows a clear QRS rhythm is also non-shockable.

Generally speaking, there is a continuum from coarse VF to fine VF to asystole. The boundary between fine VF and asystole may be set, for example, at an average amplitude of approximately 0.08-0.2 mV. A shockable VT rhythm, on the other hand, may be characterized by a heart rate of greater than about 160-180 bpm, but may vary from patient to patient. In general, the higher the VT rate, the more likely that the patient should be shocked. Hence, the criterion for evaluating the presence of a VT rhythm may need to be coupled with one or more other features (e.g., morphology) of the ECG waveform.

During ECG analysis, the detection of a regular beat indicative of a QRS wave will indicate that the rhythm is non-shockable. Hence, the detection of a large amplitude of short duration (R wave), for example, a narrow wave<160 nsec and a sharp slope>20 mV/sec, may indicate a QRS waveform. In addition, a normal sinus rhythm (non-shockable) typically has a high isoelectric content, characterized by a substantial proportion of signal lying within a relatively narrow isoelectric band. In contrast, a VF or VT signal typically has a substantially lower isoelectric content. Hence, for various implementations, clauses for ECG analysis may be based on the above description.

Determining whether a segment is shockable or non-shockable can be done, for example, by periodically checking (e.g., checking substantially continuously) if the criteria for a shockable or non-shockable clause defined on one or more parameters calculated from the ECG data are met by data collected up to the time point at which the check is being performed. As soon as a clause with a high NPV and PPV (also referred to as a high-accuracy clause) is satisfied, the presence of a shockable or non-shockable rhythm can be identified, and output provided, e.g. appropriate feedback can be provided to the caregiver and/or output signals to medical device(s) to be used to treat the patient accordingly.

To initiate an analysis of the ECG signal to determine shockability of the rhythm, a short initial segment length, e.g., an initial time period, is chosen to begin analysis. In some implementations, this length is one second, though the initial analysis segment length can be shorter (e.g., as short as 100 milliseconds, 500 milliseconds, etc.).

In this way, very rapid and accurate determinations of the status of the ECG rhythm can be achieved in times that are on order of magnitude faster than existing conventional commercial AED analysis algorithms. Speed of determination of the status of the ECG rhythm is an important determinant in the survival of a cardiac arrest victim. With conventional technology, the duration of ECG segment needed for proper assessment is 9-15 seconds, whereas with various implementations of the present disclosure of this technology, highly accurate determinations of ECG rhythm can be achieved in times as short as 1 second, or shorter. Such a short analysis duration enables automated ECG rhythm assessment during very brief pauses in chest compressions, such as immediately prior to the delivery of a defibrillation shock or during pauses in chest compressions when a ventilation is being delivered. Thus, no additional pauses in chest compressions are needed to determine ECG rhythm status. Pauses in chest compressions are known to lead to reduced survivability of a cardiac arrest victim.

Clauses may be defined for particular segment lengths. For instance, as mentioned in the previous paragraphs, if the criteria are met for a shockable or non-shockable clause for that particular segment length, then appropriate feedback can be provided to the caregiver and/or medical device(s) used to treat the patient accordingly. If, however, no shockable or non-shockable clauses are satisfied for that particular segment length, then the system makes the determination to extend the variable-length time segment by the one or more additional time periods. The additional time periods may be of a length different from the initial time segment. For instance, the first segment may be 500 milliseconds or 1 second, while further increments may be shorter increments than the initial segment, e.g. 1 millisecond, 10 milliseconds, 20 milliseconds, 100 milliseconds, 250 milliseconds.

For instance, if the increment duration is 20 milliseconds, the new analysis duration may be 520 milliseconds, using the same initial 500 milliseconds of ECG data along with the new 20 milliseconds of data. In such a case, at least one of the criteria for the clauses of the original 500 milliseconds of data may be modified, or new clauses may be added for the new length analysis segment (e.g. 520 milliseconds).

Alternatively, the additional time periods may be substantially the same duration as the initial period, e.g. 500 milliseconds. As before, one or more features of the new values of the variable-length time segment may be identified based on the adjusted rule set corresponding to the new adjusted time period, for updating the determination of whether the patient is in a shockable or non-shockable state.

In this way, the minimum amount of time will be spent making an accurate assessment of ECG rhythm status for each particular rhythm subclass.

Because the periodic checking can be conducted with a high degree of temporal granularity (e.g., 1 millisecond, 10 milliseconds, 20 milliseconds, 100 milliseconds, 250 milliseconds) or otherwise in a substantially continuous manner, for some instances, a shockable rhythm or pattern can be identified quickly (e.g., faster than conventional analysis methods), without having to wait for up to 15 seconds of ECG data. As further provided herein, for various implementations, an ECG signal may be processed according to a variable-length time segment where, if needed to reach a particular threshold of accuracy or level of prediction tested against a comprehensive patient database, the initial time period of analysis may be extended by small increments of time to determine whether the patient is in a shockable or non-shockable state.

In the current state of the art for ECG algorithms for the assessment of shockable/non-shockable rhythm status, e.g. the ECG analysis of whether a patient should be treated with a defibrillating shock, systems are focused on sensitivity and specificity and achieving high values of both sensitivity and specificity at the conclusion of fixed time intervals. For instance, typical AED ECG analysis intervals are fixed at three seconds in duration, with at least two consecutive intervals being required before a shock-no shock determination is made. Sensitivity may be characterized as the percentage of people to whom a defibrillating shock should be administered and who are correctly identified as such. The specificity may be characterized as the percentage of people to whom a defibrillating shock should not be administered, and correctly identified. In the current state of the art, data is collected for at least 6 seconds so that BOTH sensitivity AND specificity are in excess of 90%. Usually, specificity is required to be well in excess of 95%, with sensitivity required to be greater than 92-95%. This desired combination of high sensitivity and specificity can be described in the well-known to those skilled in the art, receiver-operator curve (ROC) area under the curve (AUC), where, to achieve a high ROC AUC, both values must be high.

Sensitivity or true positive rate (TPR) is given by:

$$TPR=TP/P=TP/(TP+FN)$$

Specificity (SPC) or true negative rate (TNR) is given by:

$$SPC=TN/N=TN/(TN+FP)$$

It can be seen in the equations above that heightened sensitivity may come at the expense of elevated false positives, and heightening specificity may come at the expense of false negatives, and therefore accuracy has conventionally required the combined measure of both sensitivity and specificity, resulting in longer analysis times, in excess of 6-9 seconds.

In contrast, implementations of the present disclosure focuses on accuracy as exemplified by NPV and PPV as the more relevant measures for output by the system in order to greatly accelerate determination of ECG rhythm status. As can be seen from the equations down below for PPV and NPV, the variables for PPV relate to positive predictions (e.g. "Shock advised") and the variables for NPV relate to negative predictions (E.g. "No Shock Advised"). Thus, if a positive decision results in a high PPV, it can be considered a "good decision," and if a negative decision results in a high NPV, it can also be considered a "good decision." This is not the case for sensitivity and specificity. In implementations presented herein, negative decisions are made with the minimum amount of ECG data segment length needed to achieve a high NPV or other measure similar to NPV that measures the accuracy of a negative prediction; and positive decisions are made with the minimum amount of ECG data segment length needed to achieve a high PPV or other measure similar to PPV that measures the accuracy of a positive prediction.

Positive Predictive Value is given by:

$$PPV=TP/(TP+FP)$$

Negative Predictive Value is given by:

$$NPV=TN/(TN+FN)$$

Accuracy (ACC) is given by:

$$ACC=(TN+TP)/(TP+FP+FN+TN)$$

A clause that has a sensitivity above a threshold is sometimes referred to as a high-sensitivity clause. A clause that has a specificity above a threshold is sometimes referred to as a high-specificity clause. A high-accuracy is one where either the NPV or PPV is high; in terms of sensitivity and specificity, a high accuracy clause requires BOTH the sensitivity AND specificity to be high. Because of the aforementioned equations for accuracy, sensitivity and specificity, clause limited to either high sensitivity or high specificity alone is not necessarily a high accuracy clause. In determining accuracy, the area under the curve (AUC) for the associated receiver operator curve (ROC), as known to those skilled in the art, combines sensitivity and specificity into a single measure of discriminating power of the detection algorithm.

While a technique that uses a voting scheme based on analyzing segments of predetermined length, described in more detail below, may take at least six seconds to make a determination of whether a patient is in a shockable state, in contrast, in some cases, fast-analysis techniques in accordance with the present disclosure based on high-accuracy clauses can be used to make a determination in less than the six seconds typical of a conventional voting-only technique. In emergency resuscitation situations where administering treatment sooner than later may be critical for patient survival, fast-analysis techniques provided herein may lead to potentially life-saving reduction in time delays. Multiple high-accuracy clauses can be identified via pre-validating candidate clauses over a large database of patient data, thereby allowing the identified clauses to be used with a high degree of confidence in fast identification of shockable rhythms.

Though, it can be appreciated that a voting scheme can still be used in the event that a determination cannot be made based on evaluation of the clauses alone. In some implementations, a voting scheme may be used in conjunction with techniques provided herein based on high-accuracy clauses. For example, if a clause is satisfied within a short time period (e.g., half a second), the analysis may be continued until another clause is satisfied. This can allow, for example, the use of relatively low sensitivity clauses without compromising on the accuracy of determination.

As will be described in more detail below, these techniques can be used to determine whether a patient is in a shockable or non-shockable state based on ECG time segments of variable length. An ECG time segment is a portion of an ECG signal. In contrast to a fixed-length technique, in which the length of a time signal being used to make a determination is chosen in advance of the analysis, when using a variable-length technique, the length of the signals used to make the determination are not known or otherwise predetermined in advance of the analysis. Instead, multiple time segments, at least some of which having different length than others, may be used as appropriate to complete the analysis in making a decision of shockability as quickly as possible. In addition, the length of the segments may depend on which clauses are used. Some clauses may use shorter or longer time segments than other clauses, depending on, for example, which features of the signal are used to evaluate a particular clause, and/or depending on the values of parameters used to evaluate the clauses. In this way, the length of the time segment being processed may vary based on the identity of the features being used to make the determination.

In a typical scenario, a caregiver (sometimes referred to as a rescuer) applies electrodes of a defibrillator to a patient. The defibrillator then collects ECG data, sometimes concurrent with a CPR treatment applied to the patient by the caregiver, or at times upon completion of a CPR treatment cycle or in between CPR treatment cycles. The defibrillator collects and processes ECG data by evaluating clauses against time segments of the collected data. If at least one high-confidence clause is met, the defibrillator uses the state indicated by the clause (e.g., shockable or non-shockable) to direct the caregiver, or the defibrillating device itself, to administer a shock. Sometimes, a shockable state may be identified in less than 6 seconds and sometimes within 2-3 seconds, within 1 second or less of the patient entering the state based on results of applying the clauses to the time segments of data. (Other times, a three-step voting scheme employing fixed-length time segments predetermined prior to analysis is used, which may take at least 6-9 seconds or more to identify the patient's current state.)

In some examples, the caregiver may halt the CPR treatment (e.g., due to express instruction to halt CPR treatment, during the natural course of repetitive CPR treatment, and/or during ventilations) while some of the data after completion of CPR treatment is being collected and analyzed for further confirmation of an initial determination of whether the rhythm is shockable or not shockable. Confirmation of an initial determination of shockability is sometimes referred to as a reconfirmation mode (described further below) which may allow for filtered, eliminated or otherwise reduced CPR artifact in the signal during analysis, but it may pose a potential danger to the patient depending on how long the CPR treatment is halted. Thus, if the evaluation of clauses against time segments of the data is successful in determining the state of the patient after a relatively short amount of time, e.g., less than 6 seconds, the CPR treatment can resume relatively quickly, reducing risk to the patient.

To provide further context, the heart relies on an organized sequence of electrical impulses to beat effectively. Deviations from this normal sequence is known as "arrhythmia." Certain medical devices include signal processing software that analyzes electrocardiography (ECG) signals acquired from a medical patient (e.g., a victim at a scene of an emergency) to determine when a cardiac arrhythmia such as ventricular fibrillation (VF) or shockable ventricular tachycardia (VT) exists. These devices include automated external defibrillators (AEDs), ECG rhythm classifiers, and ventricular arrhythmia detectors. An AED is a defibrillator—a device that delivers controlled electrical shock to a patient—while being relatively easy to use, such as by providing verbal prompts to a provider of care to "talk" the provider through a process of evaluating a patient for, attaching the patient to, and activating, AED therapy. The medical devices can also be configured to distinguish between a number of cardiac waveforms, such as VT and VF.

As discussed herein, VT is a tachydysrhythmia that originates from a ventricular ectopic focus, characterized by a rate that is typically greater than 120 beats per minute and wide QRS complexes. VT may be monomorphic (typically regular rhythm originating from a single focus with identical QRS complexes) or polymorphic (unstable, may be irregular rhythm, with varying QRS complexes). Depending on the rate and the length of time that the VT has been sustained, a heart in the VT state may or may not produce a pulse (e.g., pulsatile movement of blood through the circulatory system). The cardiac activity in the VT state still has some sense of organization. If there is no pulse associated with this VT rhythm, then the VT is considered to be unstable and a life threatening condition. An unstable VT can be treated with an electrical shock or defibrillation.

Supraventricular tachycardia (SVT) is a rapid heartbeat that begins above the heart's lower chambers (the ventricles). SVT is an abnormally fast heart rhythm that begins in one of the upper chambers of the heart (atria), a component of the heart's electrical conduction system called the atrioventricular (AV) node, or both. Although SVT is rarely life-threatening, its symptoms, which include a feeling of a racing heart, fluttering or pounding in the chest or extra heartbeats (palpitations), or dizziness can be uncomfortable.

VF is usually an immediate life threat. VF is a pulseless arrhythmia with irregular and chaotic electrical activity and ventricular contraction in which the heart immediately loses its ability to function as a pump. VF is the primary cause of sudden cardiac death (SCD). A VF waveform does not have a pulse associated with it. The corrective action for this rhythm is to defibrillate the heart using an electrical charge.

A normal heart beat wave starts at the sinoatrial node (SA node) and progresses toward the far lower corner of the left ventricle. A massive electrical shock to the heart can correct the VF and unstable VT rhythms. This massive electrical shock can force all the cardiac cells in the heart to depolarize at the same time. Subsequently, all of the cardiac cells go into a short resting period. The hope is that the sinoatrial node (SA node) will recover from this shock before any of the other cells, and that the resulting rhythm will be a pulse-producing rhythm, if not normal sinus rhythm.

Many AEDs implement algorithms to recognize the VT and VF waveforms by performing ECG analyses at specific times during a rescue event of a patient using defibrillation and cardio-pulmonary resuscitation (CPR). The first ECG analysis may be initiated within a few seconds after the defibrillation electrodes are attached to the patient, or after a cycle of CPR treatment has been administered. Subsequent ECG analyses may or may not be initiated, based upon the results of the first analysis. Typically, if the first analysis detects a shockable rhythm, the rescuer is advised to deliver a defibrillation shock. Following the shock delivery, a second analysis can be initiated automatically to determine whether the defibrillation treatment was successful or not (e.g., the shockable ECG rhythm has been converted to a normal or other non-shockable rhythm). If this second analysis detects the continuing presence of a shockable arrhythmia, the AED advises the user to deliver a second defibrillation treatment. A third (and possibly fourth, fifth, etc.) ECG analysis may then be executed to identify if a shockable rhythm persists, and the rescuer advised accordingly to deliver additional defibrillation treatment.

Referring now to FIG. 1, an AED 100 is shown that may be used to provide a defibrillation shock to a victim or patient at an appropriate time. FIG. 1, which shows an example implementation, depicts a rescuer using an AED 100 to automatically monitor a victim during cardiac resuscitation. The AED 100 uses measured ECG signals to monitor the victim's heart, and charges the defibrillation device within the AED. In some implementations, the AED can be configured to provide feedback (e.g., using a display device or speaker) to the rescuer if a shockable rhythm exists. Using the technology described herein, the determination whether a shockable rhythm exists can be performed significantly faster than charging process of the defibrillation device, such that the rescuer is ready with a decision to administer a shock by the time the defibrillation device is armed and ready.

In some implementations, if the AED 100 detects a dangerous heart rhythm, the AED 100 generates an alarm signal for notifying the rescuer of the condition. The AED 100 can generate a defibrillating shock to the victim when the rescuer issues a command to the AED 100 directing such a shock. The defibrillating shock is intended to remedy the dangerous rhythm of the victim's heart. In this document, heart rhythms that may be remedied via such defibrillating shocks are referred to as shockable rhythms.

The AED 100 also includes a charging module that is configured to charge the AED. In some implementations the AED 100 can be adaptively charged based on monitored ECG signals. For example, the defibrillator can be pre-charged only if a shockable rhythm is likely to exist as determined by analysis of the monitored ECG signals. In another example, the level of charge for the device can be determined and set based on the monitored ECG signals. In some implementations, the method of charging (e.g., the rate of charge, time of charging relative to the resuscitation process) can be varied based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer. An early identification of shockable rhythms, as may be facilitated by the technology described herein, may be used in determining the method of charging. For example, a fast charging process can be triggered upon identification of a shockable rhythm, thereby further reducing potentially life-threatening delays in administering a shock. On the other hand, if a shockable rhythm is not detected, the AED 100 can be charged more slowly in order to achieve power savings. Or, if it appears that an ECG rhythm may be shockable, but is not yet confirmed, the defibrillator may preemptively begin charging in case the rhythm does turn out to be shockable. This feature may be useful when ECG analysis occurs during chest compressions or during reconfirmation mode, where a short time period of analysis after chest compressions is used to confirm the existence of a shockable rhythm that had been detected during chest compressions. In such a case, the defibrillator may begin charging during the administration of chest compressions so that the defibrillator is readily able to deliver a shock once the presence of a shockable rhythm is confirmed.

The AED 100 can be configured to use a rhythm advisory method for one or more of the following: a) quantifying various features (e.g., frequency-domain features) of the ECG signals, b) differentiating normal and abnormal ECG rhythms, such as VF, c) detecting an onset of abnormal ECG rhythms, and d) making decisions about the physiological states of the heart. Analog ECG signals can be converted to data that can be analyzed using one or more processors. Such data may be referred to as "ECG data," a term which in this document is used interchangeably with the term "ECG signals." Once the AED 100 identifies the presence of a shockable rhythm based on ECG data, a display (or another output device) of the AED 100 can be used to communicate an appropriate message to the rescuer.

In some examples, one or more therapeutic delivery devices 110 can be connected to the AED 100. The therapeutic delivery devices 110 can include, for example, a portable chest compression device, a drug infusion device, a ventilation device and/or a device that can administer multiple therapies such as defibrillation, chest compression, ventilation and drug infusion. The therapeutic delivery devices 110 may be physically separate from the defibrillator AED 100, and controlled via one or more communication link 120. The communications link 120 can be a wired link (e.g., a cable) or a wireless link (e.g., a Bluetooth® or Wi-Fi link).

In some implementations, at least a portion of the control and coordination of the overall resuscitation process, and/or delivery of the various therapies may be performed in conjunction with a device 130 or processing element that is external to the AED 100. For instance, the device 130 may download and process the ECG data from the AED 100, e.g., to implement the fast detection of shockable rhythms as described herein. The device 130 can also be configured to analyze the ECG signals, perform relevant determinations like those discussed above and below based on the analysis, and control the other therapeutic devices 110, including the AED 100. In other implementations, the AED 100 may perform all the processing of the ECG, including analyzing the ECG signals, and may transmit to the control device 130 a final determination of the appropriate therapy, whereupon the control device 130 performs the control actions on the other linked devices 110.

Figure 2:
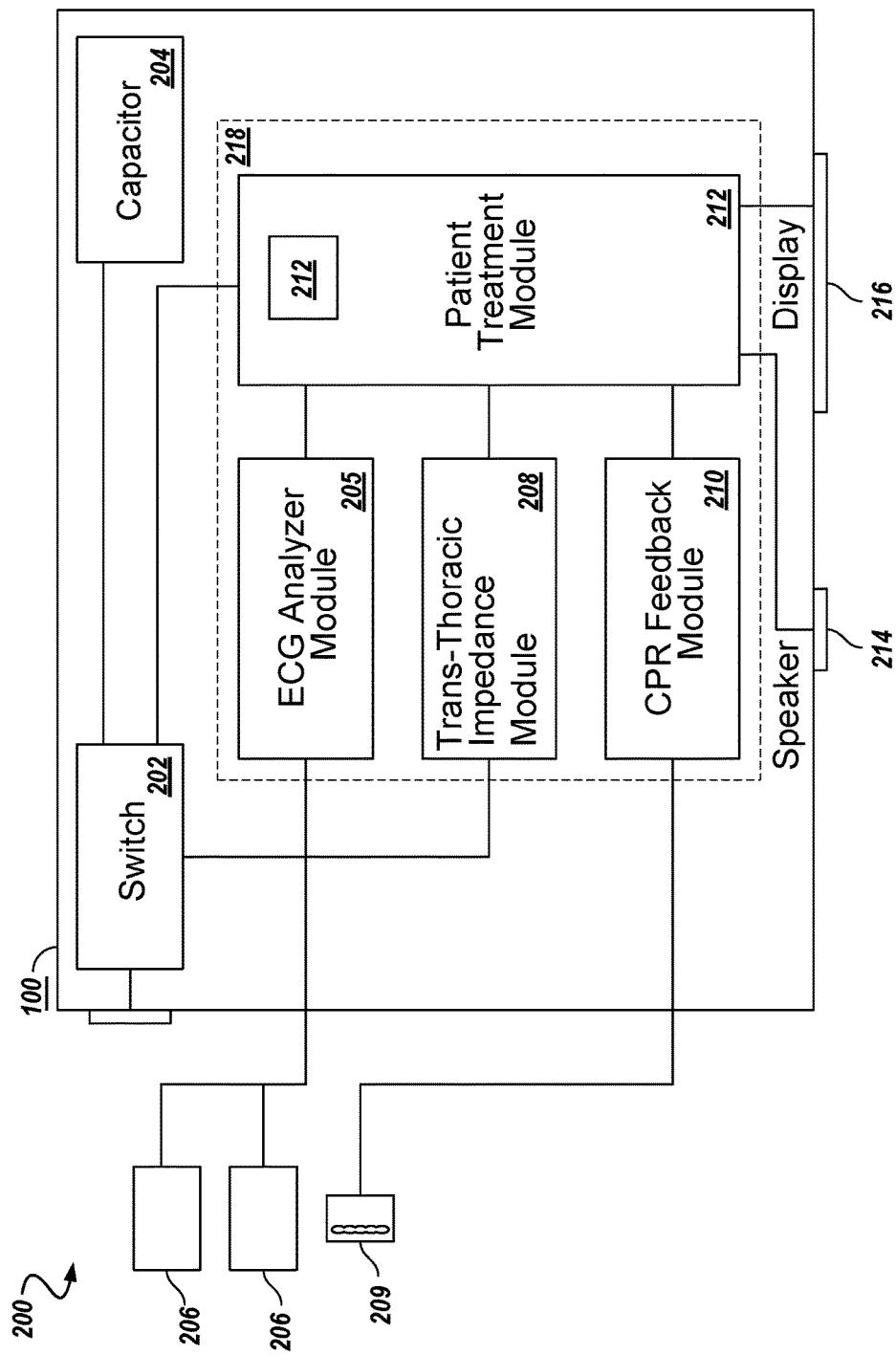
FIG. 2 is a block diagram that shows a defibrillator with an electrode package and compression puck.

Referring now to FIG. 2, a schematic block diagram 200 shows an example of the defibrillator 100, which includes a set of electrodes 206 and a compression puck 209 (e.g., to measure depth of chest compressions during a CPR treatment). In general, the defibrillator 100, and optionally one or more of the electrodes 206 and compression puck 209, defines an apparatus for administering care to a patient, subject, or individual (e.g., the victim) who requires cardiac assistance.

The AED 100 includes a switch 202 and at least one capacitor 204 for selectively supplying or applying a shock to a subject. The defibrillator further can also include an ECG analyzer module 205, a trans-thoracic impedance (TTI) module 208, and a CPR feedback module 210. The CPR feedback module 210 can be used, for example, for controlling the frequency and magnitude of chest compressions applied to a subject, and the TTI module 208 can be used for analyzing transthoracic impedance (e.g., as received via a measured TTI signal) of the patient. The AED 100 also includes input/output modules such as one or more speakers 214, and one or more displays 216.

The AED 100 also includes a patient treatment (PT) module 212. The PT module 212 can include one or more processors, and can be configured to receive inputs from one or more of the ECG analyzer module 205, TTI module 208, and CPR feedback module 210. The PT module 212 may use inputs from at least the ECG analyzer module 205 for performing various functions, e.g., determining whether or not a shockable rhythm is present in the analyzed ECG data. Even though FIG. 2 shows the ECG analyzer module 205 as a separate entity from the PT module 212, the two modules may be implemented as a single module. The PT module 212 can be configured to access a memory device (e.g., a hard drive or a random access memory or flash memory or another kind of memory device) to access representations of one or more clauses for determining the presence of a shockable rhythm. The PT module 212 can also include a buffer 213 for accumulating or otherwise holding incoming ECG data that the PT module 212 (or the ECG analyzer module 205) accesses in order to calculate one or more parameters for the accumulated data. In some implementations, the buffer 213 is a separate component from the PT module, or the buffer 213 is integrated with one of the other components described here, such as the ECG analyzer module 205. The PT module 212 can then determine whether a high-accuracy clause defined using the one or more parameters is satisfied, in order to determine whether a shockable rhythm exists. Upon determination that a shockable rhythm exists, the PT module 212 can send a control signal to one or more output devices (e.g., the speaker 214 and/or display 216) to cause alerts to be presented on the corresponding output devices.

In this example, the ECG analyzer module 205, TTI module 208, CPR feedback module 210, and patient treatment (PT) module 212 are grouped together as a logical module 218, which may be implemented by one or more computer processors. For example, respective elements of the logical module 218 can be implemented as: (i) a sequence of computer implemented instructions executing on at least one computer processor of the defibrillator 100; and (ii) interconnected logic or hardware modules within the defibrillator 100.

In the example of FIG. 2, the electrode package 206 is connected to the switch 202 via port on the defibrillator 100 so that different packages may be connected at different times. The electrode package may also be connected through the port to ECG analyzer module 205, and TTI module 208. The compression puck 209 is connected, in this example, to the CPR feedback module 210. In one implementation, the ECG analyzer module 205 is a component that receives an ECG signal. Similarly, the TTI module 208 is a component that receives a signal indicative of transthoracic impedance. Other implementations are possible. For example, the functionality of the modules 205, 208, and 210 may be combined or distributed in different manners. Further the signals received by the modules may be differently distributed.

Figure 3:
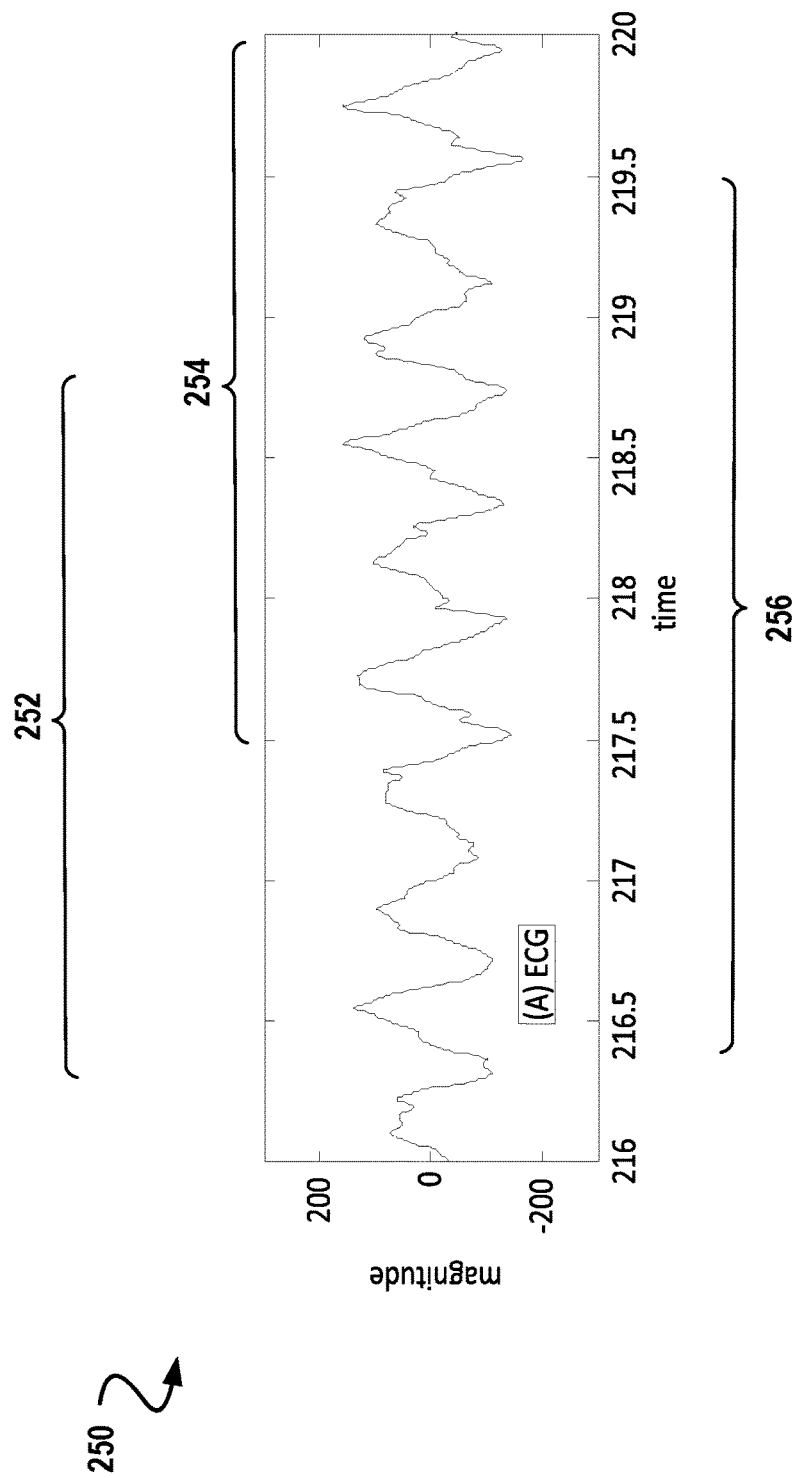
FIG. 3 is a representation of an ECG signal.

In some implementations, the PT module 212 (possibly in conjunction with other portions (e.g., ECG analyzer module 205) of the logical module 218) can be configured to process incoming ECG waveforms to determine the presence or absence of shockable rhythms. FIG. 3 shows an example of an ECG waveform 250 representing ECG data that can be processed by the ECG analyzer module 205 and PT module 212. In some examples, presence or absence of shockable rhythms is determined based on characteristics of time segments of the ECG waveform 250. For example, in FIG. 3, three time segments 252, 254, 256 of varying length, each representing a portion of about three seconds of ECG data, can be used. One of the time segments 252 can be used to determine that a clause is met, e.g., based on characteristics of the time segment 252 that correspond to values of parameters used to evaluate the clause. A different time segment 254 can be used to determine that a clause is met, which may be the same clause applied to the first time segment 252, or a different time segment (e.g., overlapping or altogether separate). If evaluation of clauses against the three time segments indicates that a shockable rhythm is present, a caregiver and/or medical device can be alerted. While three time segments are shown in this example, other examples may use just one time segment to make the determination at a particular time, or two time segments, or another number of time segments.

Figure 4A:
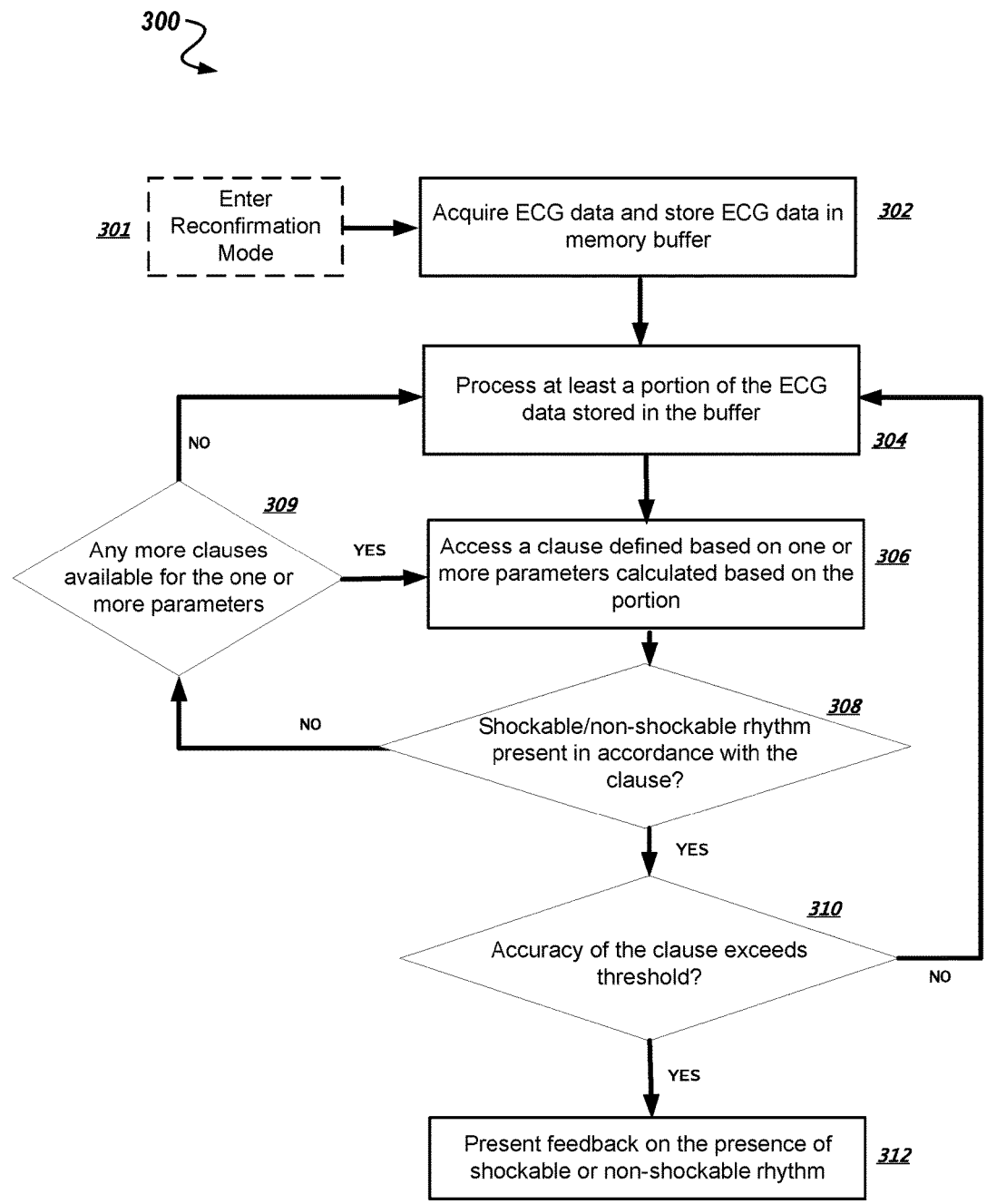
FIG. 4A shows a flowchart of an example process for identifying a presence of a shockable rhythm in ECG data.

FIG. 4A shows a process flowchart 300 of an example process for identifying a presence of a shockable rhythm in ECG data. The process can be implemented, for example, by the logic module 218 shown in FIG. 2, and applied to ECG data like the data represented by the ECG waveform 250 of FIG. 3.

The process 300 includes acquiring and storing 302 ECG data in a memory buffer. The memory buffer can be a storage device configured to store or hold data based on the ECG signals collected by the electrodes 206 (FIG. 2). For example, the ECG signals collected by the electrodes 206 can be quantized and digitized (e.g., using an analog to digital converter [ADC]) and stored in the memory buffer. The memory buffer can be configured to store a plurality of ECG segments on a first-in-first-out (FIFO) basis. For example, the ECG signals can be analyzed as they enter the buffer. In some examples, the signal can be analyzed using approximately 2-3 seconds of stored ECG signal data.

In some implementations, some or all of the ECG data being acquired is stored during a reconfirmation mode 301 of a CPR treatment, when ECG analysis occurs during CPR treatment and during a brief period after CPR treatment. In reconfirmation mode, the CPR treatment may be temporarily halted so that the CPR treatment does not affect the signal being acquired for confirming the recommendation of whether to administer a defibrillating shock. In some examples, the reconfirmation mode is terminated, and the caregiver is prompted to reconvene CPR treatment, when sufficient ECG data has been acquired.

The process 300 can include processing 304 at least a portion of the ECG data stored in the buffer. This can include processing data corresponding to a time segment of ECG signal, such that one or more features in the identified time segment is usable in determining, with at least a threshold level of accuracy, whether the patient is in a shockable state. In some implementations, this can include accessing a portion of data stored in the buffer and calculating one or more parameters based on the accessed portion of the data. These parameters are then used on a table or other database of clauses to determine whether a shockable rhythm (or a non-shockable rhythm) can be identified based on the accessed portion of the data. The length of the time segments processed will vary depending on the parameters evaluated in a particular instance of processing.

The process 300 also includes accessing 306 a database of clauses defined based on the one or more parameters calculated based on the accessed portion of the data. These clauses are defined such that various combinations of the one or more parameters can be used to identify, within the corresponding portion of the ECG signal, the presence of specific categories of ECG waveforms that represent shockable or non-shockable states with corresponding levels of accuracy.

For some implementations, the length of the time segment of the ECG signal depends on which clause is being applied to it. For example, a clause may be stored in association with a minimum time needed to achieve a threshold accuracy, e.g., 99%. In other words, the length of the time segment of the ECG signal may vary depending on which clause is applied. As an example, one clause may require one second of ECG data to achieve an accuracy value of 99%, while another clause may require three seconds of ECG data to achieve an accuracy value of 99%. In this way, the length of time of the ECG signal may depend on the identity of the parameters being evaluated at a given time, since each clause is associated with specific parameters. The process 300 can include retrieving the time length associated with a particular clause (e.g., retrieving a value for the time length stored in data storage) and determining whether sufficient ECG data is available to apply the particular clause at the threshold accuracy value. Though, it can be appreciated that for certain implementations, a given clause may be usable to achieve a threshold level of accuracy for multiple time periods of ECG analysis.

In some implementations, the accessed clauses may be sorted based on their specificities. For example, the clauses corresponding to a given set of parameters may be sorted such that the parameters are tested against high accuracy clauses before being tested against clauses with relatively lower accuracy. Due to the high level of confidence associated with high accuracy clauses (because of the correspondingly low false positive rates), if a shockable rhythm is detected based on a high PPV clause, other clauses with lower PPV may not need to be tested, thereby reducing the overall time required for identifying the presence of a shockable rhythm. If no clauses are satisfied for that particular analysis duration, data corresponding to additional segments of ECG data may have to be processed before making a final decision on the presence or absence of shockability. That is, more time may be allotted to the ECG analysis to make a decision. For example, one or more incremental amounts of time may be added to the initial time period of ECG analysis to make a suitable decision of whether to administer a defibrillating shock. As discussed herein, the incremental amount(s) of time may depend on a number of factors, such as the type of clauses employed, ECG signal pattern, ECG analysis history, amongst others. Any appropriate incremental amount(s) of time may be added to the variable-length time segment of ECG analysis, for example, less than about 3 seconds (e.g., between 1-3 seconds, between 0.1-3 seconds), less than about 2.5 seconds, less than about 2 seconds (e.g., approximately 2 seconds, between 1-2 seconds), less than about 1.5 seconds, less than about 1 second (e.g., approximately 1 second, between 0.1-1 second), less than about 0.5 seconds (e.g., approximately 0.5 seconds, between 0.1-0.5 seconds), less than about 0.1 second, etc.

Accordingly, when it is determined that the overall time of analysis should be extended, the additional increment of time may differ from the initial time period and/or other increments. Hence, the additional increment of time(s) may be shorter or longer than the initial time period of ECG analysis. For example, the initial time period of analysis may be 0.1-3 seconds (e.g., 0.1 second, 0.5 seconds, 1 second, 1.5 seconds, 2 seconds, 2.5 seconds, 3 seconds, etc.), though, an incremental extension of time for further analysis may be 0.1-0.5 seconds, 0.5-1 second, 1-2 seconds, etc. Moreover, subsequent incremental time extensions of analysis may differ. As an example, a first incremental extension of time for analysis may be 0.1-0.5 seconds, and a subsequent incremental extension of time for analysis may be 1-2 seconds. Other combinations of time periods and incremental extensions may be possible. It can also be appreciated that, for certain cases, the additional increment of time may be substantially the same as the initial time period.

Any appropriate initial time period of ECG analysis for the variable-length time segment may be employed. For example, the initial time period of analysis may be between about 0.1-3.0 seconds, between about 0.5-1.5 seconds (e.g., approximately 1 second), between about 1.5-2.5 seconds (e.g., approximately 2 seconds), between about 2.5-3.5 seconds (e.g., approximately 3 seconds), or any other suitable period of time.

One or more clauses may make up rule sets corresponding to particular durations of time of ECG analysis for determining whether the patient is in a shockable or non-shockable state. As noted herein, the clause(s) and/or rule set(s) may be statistically determined to correspond to a certain levels of accuracy. The initial time period of ECG analysis for the variable-length time segment may apply an initial rule set (involving a set of clauses, such as high accuracy clauses) where various features of the ECG signal within the initial time period are assessed to determine whether the rhythm is shockable or non-shockable, or whether the variable-length time segment should be extended for a suitable decision to be made. By extending the variable-length time segment (e.g., incrementally), an adjusted rule set (involving an adjusted set of clauses, e.g., clauses that require longer durations than the initial high accuracy clauses) may be applied to the adjusted time period, for further assessing various features of the ECG signal within the adjusted time period to determine whether the rhythm is shockable or non-shockable, or whether more time is needed to make a decision. This process may be repeated (e.g., iteratively) until a suitable decision is made as to whether the patient is in a shockable or non-shockable state.

In some implementations, a voting scheme can be employed to determine the presence or absence of shockability using clauses that do not have a high accuracy. A voting scheme uses fixed-length time segments, and not, for example, variable-length time segments (e.g., that are capable of varying depending on which of several clauses are applied to the data, or which may be divided into multiple voting segments). For example, data corresponding to three separate segments of ECG data can be processed to label the segments as either shockable or non-shockable, and the final decision can be based on the labels corresponding to at least two of the three labels. If the first two segments are labelled as shockable, the voting scheme can be terminated and the presence of a shockable rhythm can be identified. If the first segment is labelled as shockable and the second is labeled as non-shockable, a third segment is evaluated. In such a voting scheme, each segment is typically of fixed length, e.g., three seconds. Thus, when only using such a voting scheme, a minimum amount of time elapses before a determination can be made of whether a patient is in a shockable or non-shockable state. For example, if three-second segments are used, at least six seconds, and up to nine seconds, elapses before a determination can be made.

In contrast, in some implementations, the delay inherent in a voting scheme can be avoided, for example, by using high-accuracy clauses n determining the presence or absence of shockable rhythm. High accuracy (e.g., low false positive rate) clauses may be created or defined in various ways. Using such high-accuracy clauses can allow for identifying the presence or absence of shockable rhythms within a short time window (e.g., less than one second) thereby reducing analysis time as compared to, for example, the analysis time associated with a voting scheme. In some implementations, the high-accuracy clauses are determined heuristically by testing various candidate clauses for accuracy against a database of pre-stored patient data to determine clauses that have low false positive rates. In some implementations, the clauses can be determined, for example, by using a machine learning process on the database to identify conditions that indicate the presence of shockable rhythms with low false positive rates.

Although the use of high-accuracy clauses tends to be faster than the use of a voting scheme, a voting scheme can still be used in certain situations, e.g., situations in which none of the high-accuracy clauses are met and thus cannot be used in making the determination of whether a patient is in a shockable or non-shockable state. In some implementations, a voting model may be employed, for example, in parallel with other (faster) analysis techniques described herein.

The clauses with a sufficient level of accuracy for a particular time segment length (hereinafter referred to as "high accuracy" clauses), as well as clauses with an insufficient level of accuracy for a particular time segment length (also referred to herein as "normal accuracy") are defined with parameters that are calculated by processing ECG data stored in the memory buffer.

In some examples, high accuracy clauses are defined as having an accuracy threshold of 99% for a particular time length (width) of a waveform. In other words, if a clause is associated with a time length of 3 seconds and has an accuracy of at least 99%, the clause is a high accuracy clause.

In some examples, a particular clause is a high accuracy clause if the clause is applied to a portion of an ECG signal meeting a threshold time length (e.g., a length associated with the particular clause) needed to achieve a certain level of accuracy. Further, the same clause may be a normal accuracy clause if the clause is applied to a portion of an ECG signal that does not meet the threshold time length, e.g., the portion of the ECG signal has a length less than the threshold. In this way, as the length of the ECG signal portion increases, accuracy tends to increase as well. Thus, there will be a minimum time segment length below which a clause is only a normal accuracy clause, and is not suitable as a high accuracy clause, but for time segment lengths longer than this minimum time length, the clause is a high accuracy clause.

For instance, there may be clauses for which the minimum time segment length is 1 second, which are termed "1-second clauses." For instance, there may be clauses for which the minimum time segment length is 2 seconds, which are termed "2-second clauses." For instance, there may be clauses for which the minimum time segment length is 3 seconds, which are termed "3-second clauses." Segments for which the minimum time length is 6 seconds are termed "6-second clauses". Some examples of these are listed in Table 1.

TABLE 1

| Clause Timing | Intended Waveforms | Clause Logic | Result |
|---|---|---|---|
| 1 second | Normal sinus rhythm (one clear peak) | Maximum_slope > 200 uv/sample and relative_flatness > 100 | No Shock |
| 1 second | Asystole (low max and min amplitudes) | Max_amplitude < 50 uv and Min_amplitude < −50 uv | No Shock |
| 1 second | Slow VT | Peaks < 3 and average_peak_width > 160 ms | No Shock |
| 1 second | PEA | Maximum_slope < 30 uv/sample and peaks < 3 | No Shock |
| 1 second | VFIB | Peaks > 3 and relative_flatness < 50 | Shock |
| 1 second | Fast VT | Peaks >= 4 and average_peak_width > 160 ms and peak_width_variability < 100 | Shock |
| 2 seconds | AFIB (many peaks but one or more tall peaks) | Maximum_slope > 200 uv/sample and relative_flatness > 80 and peak_tops_amplitude_variability < 250 | No Shock |
| 2 seconds | Slow PEA | Maximum_slope < 50 uv/sample and peak_tops_amplitude_variability < 250 and peak_tops_interval_variablity < 100 | No Shock |
| 2 seconds | VF (many peaks) | Maximum_slope > 50 uv/sample and relative_flatness < 50 and slope_zero_crossings > 20 | Shock |
| 2 seconds | VT (high rate and VT | R-R_interval < 350 ms and QRS_Width > 140 ms and QRS_Width_Variation == 1 | Shock |
| 6 seconds | VT waveform (HR > 150 bpm and wide complexes) | R-R_interval < 400 ms and QRS_Width > 140 ms and QRS_Width Variation == 1 and flatness < 50 | Shock |
| 6 seconds | irregular PEA rhythm (intermittent flat areas and wide peaks) | flatness > 200 and pos_peak_width > 300 | No Shock |

Some additional 3-second clauses are found in Table 2.

TABLE 2

| Intended Waveforms | Clause Logic | Result |
|---|---|---|
| Few sharp peaks | ((Amplitude Variability < Threshold) AND (Amplitude > 250 microvolts) AND (Maximum Slope > Threshold)) | No Shock |
| Stable HR and QRS width | ((QRS Rate > 220) AND (Width Variation == Stable) AND (Width < 100 milliseconds)) OR ((SVT) AND (QRS Rate > 245)) | No Shock |
| Stable QRS width | ((Width Variation == Stable) AND (QRS Width < 65) AND (Amplitude > 250) AND (QRS Rate > 300) | No Shock |
| Stable QRS amplitude, large QRS amplitude, clear peaks. HR > 180 | ((Amplitude Variability < Threshold) AND (Amplitude > 500) AND (Amplitude Variability <= Threshold) AND (QRS Variability < Threshold) AND (QRS Rate > 300) | No Shock |

Some additional 6-second clauses can be found in Table 3.

TABLE 3

| Intended Waveforms | Clause Logic | Result |
| --- | --- | --- |
| Asystole waveform with very small electrical activity | (Average amplitude less than 100 microvolts) | Non Shockable |
| Fast PEA type waveform where HR > 160 with some variability and stable QRS width but maximum slope is low | (QRS Rate greater than 270 BPM) AND (QRS Variability < QRSV_Threshold) AND (Amplitude Variability < AV_Threshold) AND (Maximum Slope < Min_Slope_Threshold) AND (Width Variability > WV_Threshold) | Non Shockable |
| SVT type waveform, Number of SVT beats exceeds threshold, heart rate < 185, QRS width < 140 ms | ((SVT Beats Detected) OR ((NUMBER_OF_SVT_BEATS > SVT_CNT_Threshold) AND (QRS_Rate > QRS_Rate_Threshold) AND (QRS_Widh < QRSW_Threshold)) OR ((NUMBER_OF_SVT_BEATS > SVT_CNT_Threshold) AND (QRS Rate > QRS Rate Threshold 2) AND (QRS_Width < QRS Width Threshold)) | Non Shockable |

In accordance with various implementations described herein, the defibrillator begins by analyzing as shortest interval clause available, for example the 1-second clauses in the example above. This shortest interval may, however, be as short as 100 milliseconds. If, after analyzing the ECG in the shortest segment to determine if the ECG measurements or features meet any one of those shortest segment clauses rule sets, it is found that the criteria of none of the clauses or rule sets are met, then the initial time period is extended and the clauses or rule sets for the shorter interval are adjusted to provide a predetermined adequate level of accuracy for the shock/no-shock determination for the extended time interval. The clause adjustments may take the form of relatively minor modifications of threshold values, or, alternatively, adding new clauses or sub-clauses to maintain adequate accuracy for the different time interval of analysis. Examples of such clauses can be found in Tables 1, 2, and 3.

In one example, the time extension is one second intervals, as in the description above, e.g. 1-second, 2-second, 3-second clauses, or alternatively may be 3 seconds, as in the case of 3-second and 6-second clauses. Alternatively, the time extension increments may be sub-divisions of the minimum increment, e.g. 0.1 second, thus yielding additional clauses of 1.1-second, 1.2-second, 1.3-second, 1.4-second, etc., clauses. In such a fashion, the defibrillator would re-analyze the ECG every sub-increment interval, e.g. 0.1 seconds, with a new shock/no-shock decision every 0.1 seconds.

The presence of a shockable or non-shockable rhythm can be determined 308 in accordance with one or more clauses. In some examples, the presence of the shockable rhythm can be determined based on a single time segment, e.g., if a single clause is met based on that time segment, and the clause is associated with a shockable state, then the determination is made based on that clause alone without requiring further analysis that would otherwise delay treatment. In some examples, at least two or three time segments are used in the determination, e.g., unless at least one clause indicating a shockable state is met for each of the two or three time segments, then clauses continue to be evaluated on the data. If a particular clause is not satisfied at a given time, a check can be performed 309 to see if other clauses defined on the calculated parameters are available to gain more information in determining whether a shock or no-shock decision should be made. If one or more other clauses that can provide this added information are available, the process includes accessing 306 the clause(s) to repeat the check for the presence of a shockable or non-shockable rhythm. On the other hand, if no other clauses are present, additional portions of the ECG data stored in the buffer can be processed 304. In some implementations, this can include repeating at least a portion of the process described above on additional ECG data that has been accumulated in the buffer since the last round of processing. In some implementations, this can include data already processed in the last round together with new data that has been accumulated. In some implementations, this can include processing data corresponding to segment that is non-overlapping with the segment processed in the last round.

Upon determining the presence of a shockable or non-shockable rhythm, the process 300 can include checking 310 if the accuracy of the satisfied clause exceeds a threshold. In some examples, the threshold is an accuracy of at least 99%. In some implementations, this check may also be performed before determining whether a shockable or non-shockable rhythm is present. If the accuracy of the clause exceeds the threshold (e.g., if the clause is a high-accuracy or high confidence clause), a feedback signal on the presence of the shockable or non-shockable rhythm may be presented to the caregiver (312), although such a feedback signal is not required (e.g., when set to a certain setting, a defibrillating shock may be automatically given without user intervention). While not required for certain instances, feedback can include generating a control signal that causes the feedback to be presented on a device (e.g., the AED 100, a mobile device associated with the caregiver, or a wearable device associated with the caregiver). The feedback can be presented, for example, in the form of a visual indication on a display screen, an audible sound presented via a speaker, or a haptic feedback presented via a wearable or mobile device. In response to the feedback, the caregiver can then choose to shock the patient, e.g., if the feedback indicates that the patient is in a shockable state. In some examples, the feedback may be provided as soon as the capacitors of the defibrillator are charged, so that the shock can be administered as soon as possible. For example, the capacitors may be charged in approximately five seconds, which may be sufficient time to determine the state of the patient using the techniques described in this document. Other, slower techniques, e.g., a technique that uses only a voting scheme based on analyzing ECG segments of predetermined durations, may use more time to make such a determination, such that there is often a delay between the time that the capacitors are charged and the time that the determination of the patient's state is made.

If the accuracy if clause does not exceed a threshold, additional portions of the ECG data stored in the buffer can be processed 304. In some implementations, this can include repeating at least a portion of the process described above on additional ECG data that has been accumulated in the buffer since the last round of processing. This can be continued until a shockable or non-shockable rhythm is determined with a desired accuracy. By processing data substantially continuously (e.g., once every few machine cycles, or a few times per second), the process 300 allows for fast detection of shockable or non-shockable rhythms in monitored ECG data. Because the processing does not depend on fixed segments of data of predetermined length, a determination can be made quickly without having to wait for the data of the predetermined length to be accumulated. By using clauses with known specificities, the process of determination can be terminated as soon as a high-confidence determination is made, thereby saving valuable time that could potentially provide life-saving benefits to patients in critical conditions.

In some implementations, determining the presence of a shockable or non-shockable rhythm using the techniques described herein can be used in place of a technique that uses only a voting scheme where a predetermined number of ECG segments are analyzed and labeled as shockable or non-shockable. The tables below show comparative performances of the two techniques based on an example set of experiments performed using the same database of patient data. In the tables below, the techniques described in this document is denoted as "fast analysis." In contrast, the voting scheme used in the comparison used up to three segments of ECG data, and is denoted in the tables below as "2 out of 3 voting."

TABLE 4

| Performance comparison | | |
|---|---|---|
| Algorithm | Sensitivity | Specificity |
| 2 out 3 voting | 99.67 | 99.86 |
| Fast Analysis | 99.67 | 99.87 |

TABLE 5

| Analysis Time Comparison | | | |
|---|---|---|---|
| Algorithm | 3 Analyses | 6 Analyses | 9 Analyses |
| 2 out 3 voting | 0% | 98% | 2% |
| Fast Analysis | 85% | 14% | 1% |

In some implementations, in a reconfirmation analysis mode (RAM), the determination of the presence of a shockable or non-shockable rhythm is performed during administration of CPR. The tables below show comparative performances of existing RAM techniques with the fast analysis techniques described in this document. In the experiments, the fast analysis was compared again RAM analysis using a database containing ECG waveform with CPR artifact following by a period of CPR free waveform.

TABLE 6

| Performance comparison | | |
|---|---|---|
| Algorithm | Sensitivity % | Specificity % |
| Fast Analysis | 97 | 99 |
| RAM | 96 | 99 |

TABLE 7

| Analysis Time Comparison | | | |
|---|---|---|---|
| Algorithm | 3 Second Analyses | 6 sec. Analyses | 9 sec. Analyses |
| Fast Analysis | 76% | 22% | 2% |
| RAM Analysis | 62% | 36% | 2% |

In some implementations, the RAM analysis may be combined with the fast analysis described herein. In such an analysis, the high-accuracy clauses can be given higher priority over analysis during CPR. In a particular set of experiments, three second post-CPR segments were analyzed to calculate the parameters. If the parameters satisfied a high confidence clause, results from analysis during CPR results were ignored and the high-accuracy clause was used for the final decision. The results for the particular set of experiments are provided in the tables below.

TABLE 8

| Performance | | |
|---|---|---|
| Algorithm | Sensitivity % | Specificity % |
| RAM + FAST Analysis | 96 | 99 |

TABLE 9

| Analysis Time | | | |
|---|---|---|---|
| Algorithm | 3 Second Analyses | 6 sec. Analyses | 9 sec. Analyses |
| RAM + FAST Analysis | 87% | 12% | 1% |

Figure 4B:
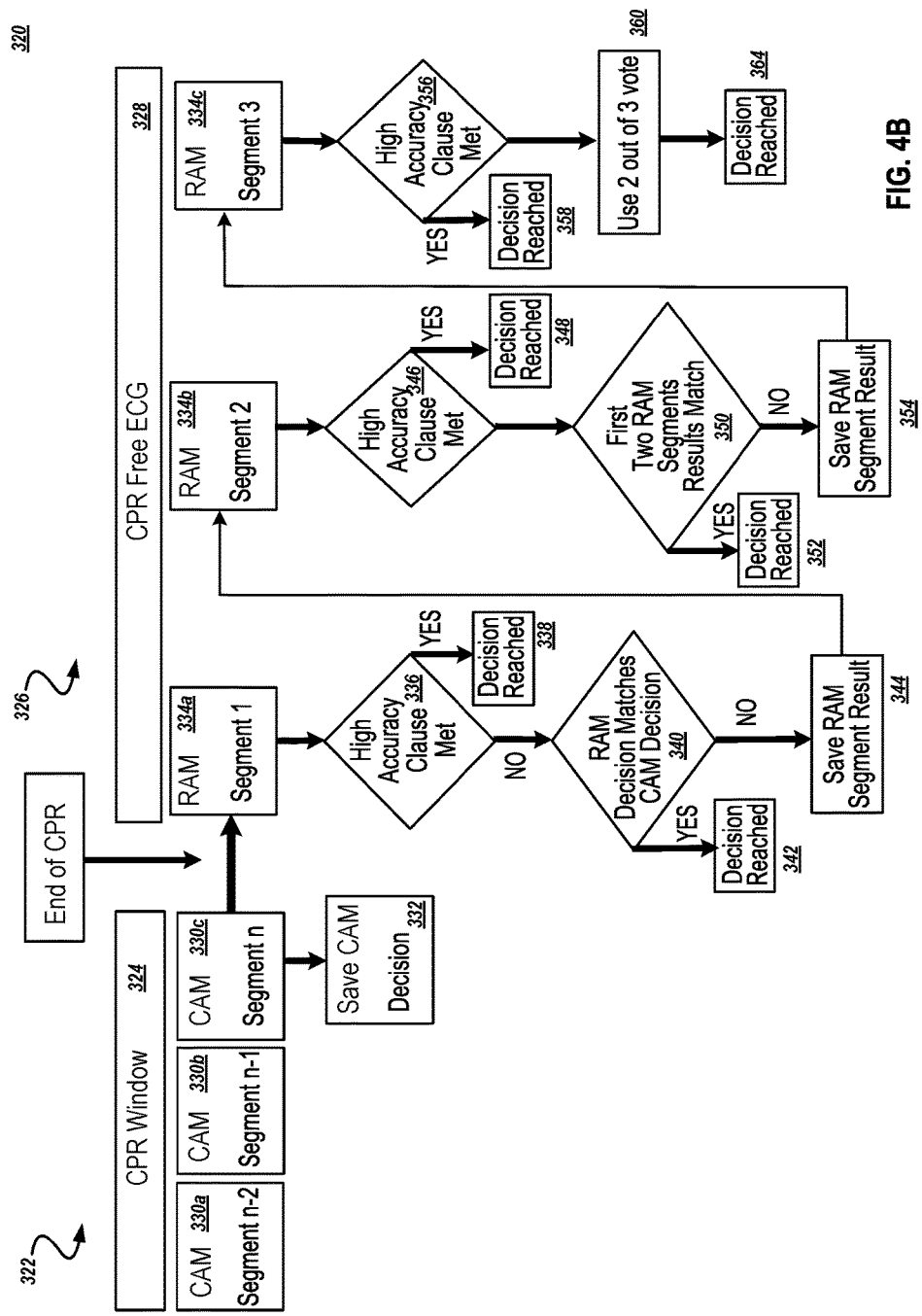
FIGS. 4B-4C show example schematics for identifying a presence of a shockable rhythm in ECG data.

FIG. 4B shows a diagram representing a technique 320 for determining whether a patient is in a shockable or non-shockable state based on an ECG signal measured from the patient, according to either a voting process or whether a high accuracy clause is met before the voting process is complete. As described above, a high accuracy clause is a clause that exhibits a high predictive certainty based on PPV (positive predictable values) and/or NPV (negative predictive value). The technique 320 can be implemented as functionality of a defibrillator, e.g., the AED 100 shown in FIG. 1.

The technique 320 includes two modes. The first mode 322, which is an optional mode, sometimes referred to as "Continuous Analysis Mode" (CAM), includes a CPR window 324 in which measurements are taken while CPR (chest compressions) is being applied to the victim. The second mode 326, sometimes referred to as "Reconfirmation Analysis Mode" (RAM), is performed during a CPR-free window 328, e.g., during which time CPR (chest compressions) is not applied to the victim. In some examples, the application of CPR can interfere with detecting a "clean" ECG signal (e.g., a signal absent substantial noise induced by the CPR treatment), so the second mode 326 can be used to detect a CPR-free signal. The technique 320 can alternate between the first mode 322 and the second mode 326, e.g., during a rescue situation. In some examples, the mode changes when the AED 100 detects that CPR has stopped or started (e.g., by detecting that the motion associated with chest compressions has stopped or started). In some examples, the mode changes when the AED 100 provides an instruction to a rescuer (e.g., using an output device such as a display or audio output device) to stop or start CPR.

In the first mode 322, an analysis of successive segments 330a-c of an ECG signal during CPR can be performed. For example, if any clauses used for ECG analysis during CPR are met by any of the segments 330a-c, a decision (e.g., CAM decision) of whether the ECG signal represents a shockable or non-shockable rhythm is saved 332 (e.g., for later comparison with an analysis during the CPR-free window to finalize the determination). The decision can be based, for example, on clauses applied to the segments 330a-c. Because analysis during CPR may be less reliable than analysis made when CPR has stopped, the saved decision can be confirmed in the second mode 326.

In the second mode 326, CPR is halted and ECG signal segments 334a-c can be analyzed absent any potential noise from the CPR treatment. A first segment 334a is analyzed, e.g., by applying 336 high accuracy clauses to the segment 334a. If the high accuracy clause is met, e.g., by indicating a shockable or non-shockable rhythm, then a decision of a shockable or non-shockable rhythm has been reached 338 and further analysis need not be undertaken. If not, other normal accuracy clauses can be applied 340 to the segment 334a. If one of the other clauses (e.g., a normal accuracy clause) is satisfied by the segment and that clause indicates the same result (e.g., a RAM decision indicating a shockable rhythm or non-shockable rhythm) as was indicated in the saved decision 332 (e.g., CAM decision) of the first mode 322, then a decision of a shockable or non-shockable rhythm has been reached 342. Put another way, because the results match, the matching result (e.g., between the CAM decision and the RAM decision) can be used as the final decision. However, if the other normal accuracy clause(s) indicate a different result as the saved decision, then the result of the other normal accuracy clause(s) is saved 344 and the technique 320 proceeds to analysis of a second segment 334b.

During analysis of the second segment 334b, high accuracy clauses can again be applied 346. If a high accuracy clause is met, e.g., by indicating a shockable or non-shockable rhythm, then a decision of a shockable or non-shockable rhythm has been reached 348 without further processing required. If not, other clauses can be applied 350 to the segment 334b. If another clause (e.g., a normal accuracy clause) indicates the same result (e.g., a shockable rhythm or non-shockable rhythm) as the saved result 344 of the analysis of the first segment 334a, then a decision of a shockable or non-shockable rhythm has been reached 352. If the other normal accuracy clause(s) indicate a different result as the saved result 344, then the result of the other normal accuracy clause(s) is saved 354 and the technique 320 proceeds to analysis of a third segment 334c.

During analysis of the third segment 334c, high accuracy clauses are again applied 356. If a high accuracy clause is met, e.g., by indicating a shockable or non-shockable rhythm, then a decision of a shockable or non-shockable rhythm has been reached 358. If not, other normal accuracy clauses can be applied 360 to the segment 334c, and a "2 out of 3" vote can occur. If another clause (e.g., a normal accuracy clause) indicates the same result (e.g., a shockable rhythm or non-shockable rhythm) as either of the saved result 344 of the analysis of the first segment 334a or the saved result 354 of the analysis of the second segment 334b, then a decision of a shockable or non-shockable rhythm has been reached 364. Put another way, when two of the three results match, those matching results (e.g., shockable or non-shockable) is used as the decision of whether the patient is in a shockable or non-shockable state.

Figure 4C:
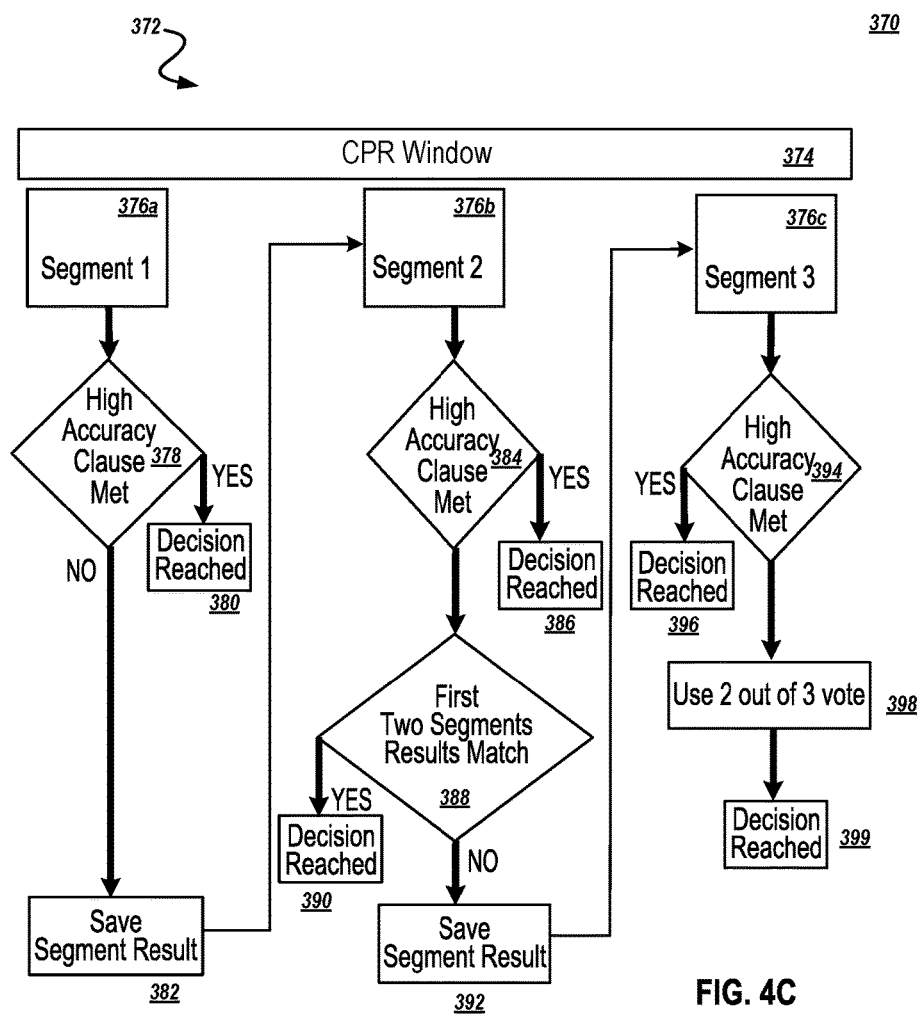

FIG. 4C shows a diagram representing a technique 370 for determining whether a patient is in a shockable or non-shockable state based on an ECG signal measured from the patient according to either a voting process or whether a high accuracy clause is met before the voting process is complete. The technique 370 can be implemented as functionality of a defibrillator, e.g., the AED 100 shown in FIG. 1.

The technique 370 includes a single mode 372 in which measurements are taken while CPR is being applied to the victim during a CPR window 374. In this mode 372, ECG signal segments 376a-c can be analyzed. A first segment 376a is analyzed, e.g., by applying 378 high accuracy clauses to the segment 376a. If the high accuracy clause is met, e.g., by indicating a shockable or non-shockable rhythm, then a decision of a shockable or non-shockable rhythm has been reached 380. If not, other normal accuracy clauses can be applied to the segment 334a. If the normal accuracy clause(s) indicate that the rhythm is shockable or non-shockable, the result is saved 382 and the technique 370 proceeds to analysis of a second segment 376b.

During analysis of the second segment 376b, high accuracy clauses can again be applied 384. If the high accuracy clause is met, e.g., by indicating a shockable or non-shockable rhythm, then a decision of a shockable or non-shockable rhythm has been reached 386. If not, other clauses can be applied 388 to the segment 376b. If the clause(s) (e.g., a non-high accuracy clause) indicate the same result (e.g., a shockable rhythm or non-shockable rhythm) as the saved result 382 of the analysis of the first segment 376a, then a decision of a shockable or non-shockable rhythm has been reached 390. If analysis employing the other clause(s) indicate a different result as the saved result 382, then the result of analysis of the other clause(s) is saved 392 and the technique 370 proceeds to analysis of a third segment 376c.

During analysis of the third segment 376c, high accuracy clauses are again applied 394. If a high accuracy clause is met, e.g., by indicating a shockable or non-shockable rhythm, then a decision of a shockable or non-shockable rhythm has been reached 396. If not, other clauses (e.g., normal accuracy clauses) can be applied 398 to the segment 376c, and a "2 out of 3" vote can occur. If the other clause(s) (e.g., normal accuracy clauses) indicate the same result (e.g., a shockable rhythm or non-shockable rhythm) as either of the saved result 382 of the analysis of the first segment 376a or the saved result 392 of the analysis of the second segment 376b, then a decision of a shockable or non-shockable rhythm has been reached 399. Put another way, when two of the results match, those matching results (e.g., shockable or non-shockable) is used as the decision of whether the patient is in a shockable or non-shockable state, based on the measured ECG signal.

Figure 4D:
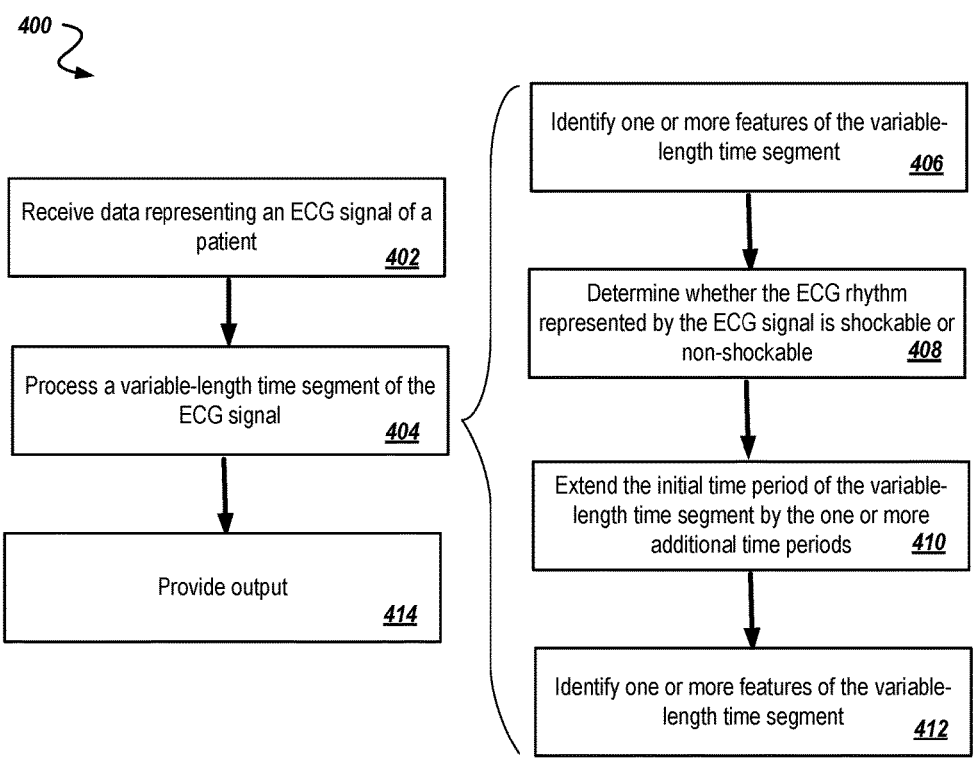
FIGS. 4D-4E show flowcharts of example processes for identifying a presence of a shockable rhythm in ECG data.

FIG. 4D shows a flowchart of an example process 400 for identifying a presence of a shockable rhythm in ECG data. The process can be implemented, for example, by the logic module 218 shown in FIG. 2, and applied to ECG data like the data represented by the ECG waveform 250 of FIG. 3.

The process 400 includes receiving 402 data representing an ECG signal of a patient, e.g., while the patient is undergoing rescue treatment. The process 400 includes processing 404 a variable-length time segment of the ECG signal. The variable-length time segment includes an initial time period (e.g., between 0.1 second and 3.0 seconds) incrementally extendable by one or more additional time periods (e.g., 0.1 second, 0.5 seconds, 1.0 second, 1.5 seconds, 2.0 seconds, 2.5 seconds, 3.0 seconds, etc.). In this way, the amount of time needed for the determination of whether the patient is in a shockable or non-shockable state is not known in advance of the determination. In some examples, the length of the time segment being processed varies based on identity of the features being used to make the determination of whether the ECG rhythm is shockable or non-shockable.

The processing includes identifying 406 one or more features of the variable-length time segment based on an initial rule set corresponding to the initial time period. In some examples, the initial rule set includes one or more clauses representing constraints on one or more features of the ECG signal, each of the one or more features of the ECG signal representing a characteristic of a waveform of the ECG signal within the processed time segment.

The processing includes, based on the initial rule set, determining 408 whether the ECG rhythm represented by the ECG signal is shockable or non-shockable or whether to extend the variable-length time segment for further analysis (e.g., if no accurate determination can be made using the initial time period). The processing includes extending 410 the initial time period of the variable-length time segment by the one or more additional time periods (e.g., 0.1 second, 0.5 seconds, 1.0 second, 1.5 seconds, 2.0 seconds, 2.5 seconds, 3.0 seconds, etc.). The processing includes identifying 412 one or more features of the variable-length time segment based on an adjusted rule set corresponding to an adjusted time period, for updating the determination of whether the ECG rhythm is shockable or non-shockable. In some examples, the initial rule set can include at least one high accuracy clause and the adjusted rule set includes at least one lower accuracy clause, such that the at least one high accuracy clause is different from the at least one lower accuracy clause.

The process 400 includes providing 414 an output based on the determination, e.g., by using an output circuit or output module (e.g., output screen, audio circuit, etc.).

In some examples, the data representing an ECG signal of a patient is received while CPR is being performed. In some examples, data representing an ECG signal of a patient while CPR has been temporarily halted. For example, the process 400 can include identifying whether an interruption in chest compressions has occurred, and analyzing the variable-length time segment of the ECG signal during the chest compression interruption according to the initial rule set. In some examples, identifying whether the interruption in chest compressions has occurred includes processing signals produced from at least one of an ECG electrode and a motion sensor.

Figure 4E:
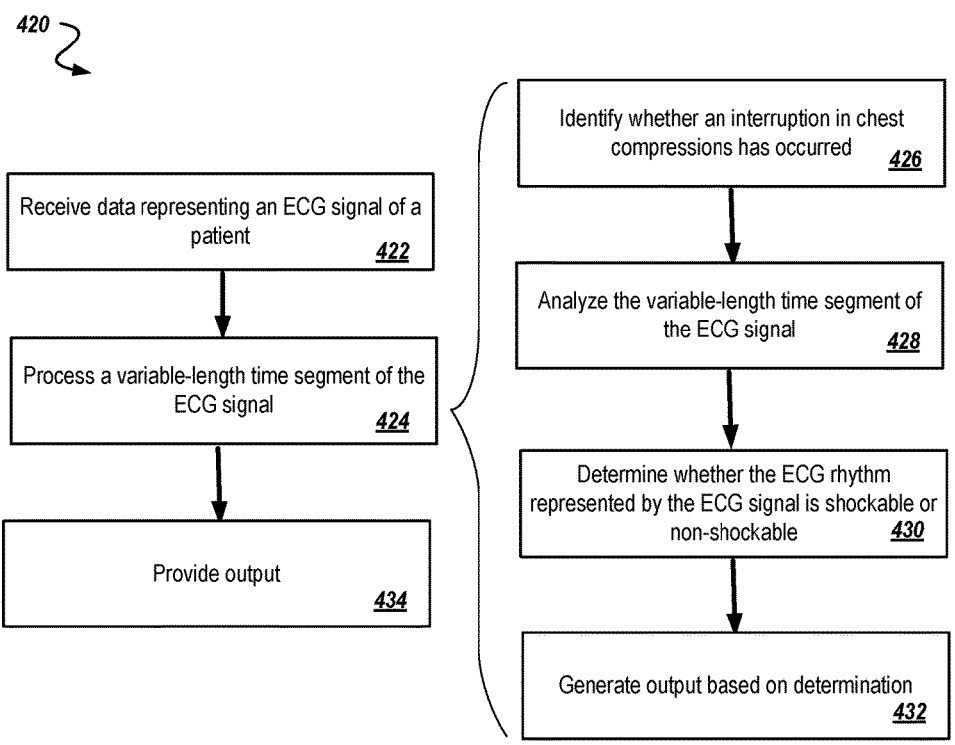

FIG. 4E shows a flowchart of an example process 420 for identifying a presence of a shockable rhythm in ECG data. The process 420 can be implemented, for example, by the logic module 218 shown in FIG. 2, and applied to ECG data like the data represented by the ECG waveform 250 of FIG. 3.

The process 420 includes receiving 422 data representing an ECG signal of a patient e.g., while the patient is undergoing rescue treatment. The process 420 includes processing 424 a variable-length time segment of the ECG signal comprising an initial time period of between 0.1 second and approximately 3 seconds. The processing includes identifying 426 whether an interruption in chest compressions has occurred, e.g., by processing signals produced from at least one of an ECG electrode and a motion sensor. The processing includes analyzing 428 the variable-length time segment of the ECG signal during the chest compression interruption according to an initial rule set based on the initial time period. The analysis can be used to determine whether an ECG rhythm represented by the ECG signal is shockable or non-shockable. In some examples, the initial rule set includes one or more clauses representing constraints on one or more features of the ECG signal, each of the one or more features of the ECG signal representing a characteristic of a waveform of the ECG signal within the processed time segment.

The processing includes, based on the initial rule set, determining 430 whether the ECG rhythm represented by the ECG signal is shockable or non-shockable or whether to extend the variable-length time segment for further analysis (e.g., if no accurate determination can be made using the initial time period). The processing includes generating 432 an output based on the determination of whether the ECG rhythm represented by the ECG signal is shockable or non-shockable. The process 420 includes providing 434 an output based on the determination, e.g., by using an output circuit or output module (e.g., output screen, audio circuit, etc.).

Figure 4F:
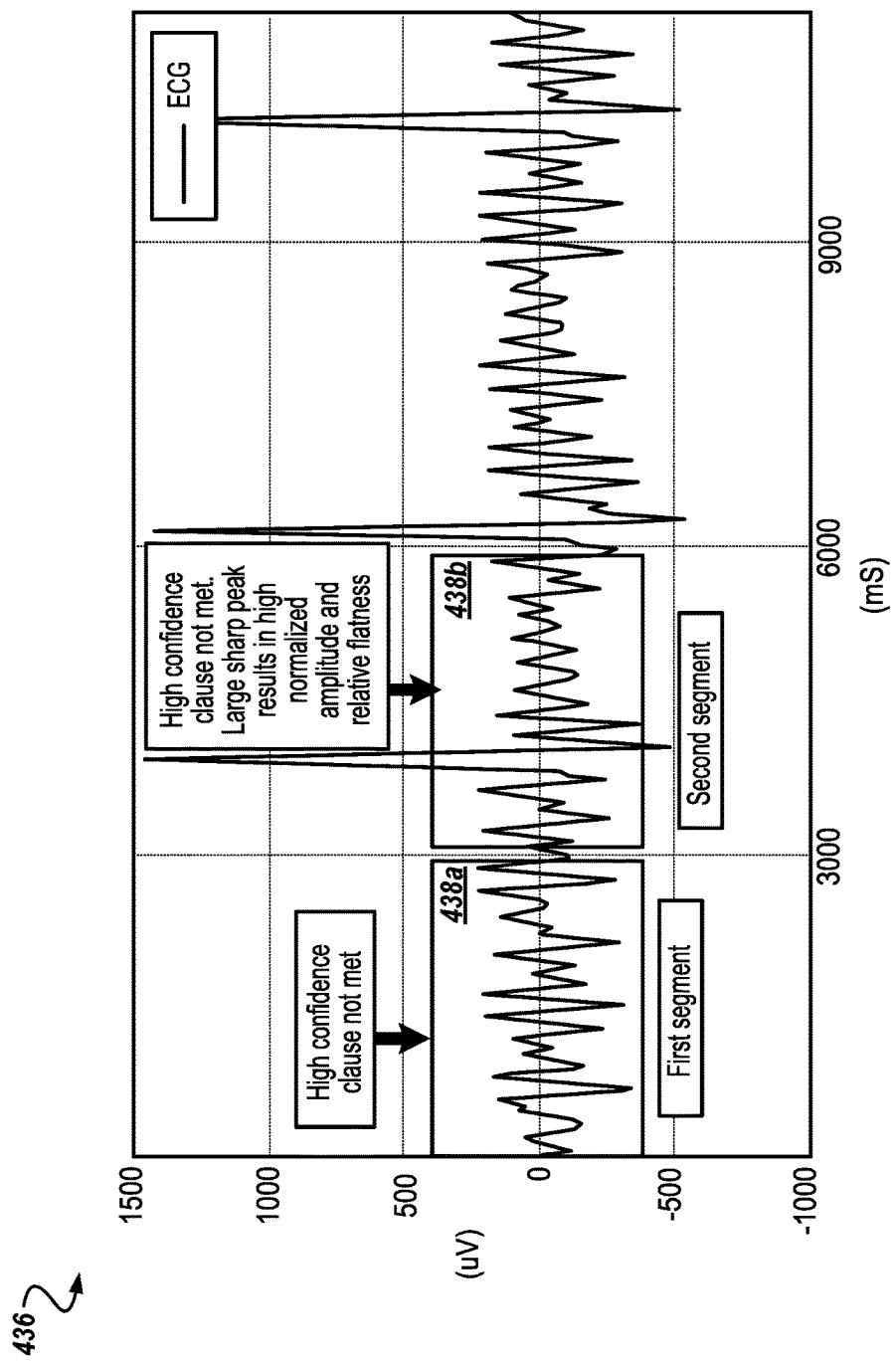
FIG. 4F shows an example of an ECG waveform.

FIG. 4F shows an example of a waveform 436 having two segments 438a-b that can be analyzed, e.g., using one of the techniques 320, 370 shown in FIGS. 4B-4C. For example, the first segment 438a does not definitively meet any high accuracy clauses, and thus an analysis, e.g., using the techniques 320, 370 would proceed to an analysis of a second segment 438b. In the example shown, the second segment 438b does definitively meet a high accuracy clause, and thus a decision can be reached based on whether the high accuracy clause indicates that the waveform 436 is shockable or non-shockable. In this case, the second segment 438b provides a stronger indication that the ECG rhythm is non-shockable.

As discussed herein, in the interest of determining whether an ECG rhythm represented by an ECG signal is shockable or non-shockable as quickly as possible, it may be preferable for gaps or interruptions in chest compressions to be analyzed as quickly and efficiently as possible. For instance, at any point whenever chest compressions have ceased, even for a short period, an ECG analysis to determine whether a rhythm is shockable or non-shockable, or to determine if more time is needed, may be appropriate. In some instances, interruptions in chest compressions may be fairly short (e.g., less than approximately 3 seconds). For instance, the rescuer may be inclined to readjust his/her position, switch roles with another rescuer, be distracted, slightly fatigued or may otherwise pause chest compressions. For such cases, since it is indeterminate as to when chest compression will recommence, it may be advantageous for the system to begin its rhythm analysis immediately, so that minimal time for determining the cardiac state of the patient is wasted. In some instances, the time period of chest compression interruption may be substantial (e.g., greater than 12-15 seconds). For example, the rescuer may be instructed to stop CPR chest compressions and wait for the defibrillating system to perform an ECG analysis, the rescuer may switch to another resuscitation activity altogether, such as ventilation, etc. In such cases, the ECG analysis may run its regular course.

For various implementations, as discussed above, the defibrillator system may be configured to begin ECG analysis as soon as it identifies an interruption in chest compressions being administered to the patient, or shortly thereafter. The defibrillator system may track chest compressions by any suitable method or technique. In some implementations, the defibrillator system incorporates a motion sensor (e.g., accelerometer, velocity sensor, displacement sensor) at a location where the rescuer is administering chest compressions, to detect the presence of the chest compressions. For example, an accelerometer may be embedded in a chest compression sensor and the rescuer may place the chest compression sensor between the patient's chest and his/her hands during CPR compressions. The acceleration signals produced by the sensor may be processed accordingly. Such a motion sensor may further be used to sense the depth and rate of chest compressions, so as to provide the rescuer with appropriate CPR feedback. Various implementations where a determination of whether a cardiac rhythm is shockable based only on time periods of the ECG signal during which there has not been CPR chest compressions delivered are described in U.S. Pat. No. 6,961,612, entitled "CPR Sensitive ECG Analysis in an Automatic External Defibrillator," which is hereby incorporated by reference in its entirety, and may be used in conjunction with systems and methods described herein.

FIGS. 4G-4L depict illustrative implementations that include schematics where the defibrillator system quickly identifies whether an interruption in chest compressions has occurred and applies an appropriate analysis algorithm. In each implementation, the respective schematics show a period of time in which CPR chest compressions are being provided. During this CPR window, as described further herein, the defibrillator system may optionally apply a continuous analysis advisory for whether a shockable or non-shockable rhythm is detected, while taking into account artifacts that arise through chest compressions. Such a continuous analysis advisory may include appropriate filtering, frequency-based analyses, and/or other suitable analysis techniques for providing an indication of whether a rhythm represented by the ECG signal is shockable or non-shockable. This indication may be used to make a determination (subsequently or at the time of analysis) of whether a defibrillating shock should be applied. For example, the continuous analysis advisory may indicate that the ECG rhythm is likely to be shockable, and such an indication may be subsequently confirmed via a subsequent hands-free ECG analysis, where CPR chest compressions are not occurring. In general, a hands-free ECG analysis may provide more accurate shock analysis than continuous ECG analysis during compressions. Examples of suitable continuous analysis advisory algorithms (while during compressions) that may be employed include those described in U.S. Pat. No. 8,706,214, entitled "ECG Rhythm Advisory Method," and U.S. Pat. No. 8,880,166, entitled "Defibrillator Display," each of which are hereby incorporated by reference in their entirety.

As discussed above, to make a final determination of whether the ECG rhythm sensed from the patient is one where a defibrillating shock should be applied, it may be necessary to stop chest compressions for a brief period to analyze a more clean ECG (e.g., without artifacts arising from CPR chest compression). Accordingly, the defibrillating system may prompt the user to stop CPR, for example, via an audio and/or visual prompting from the user interface of the defibrillator. If the user acknowledges this prompting and interrupts the process of applying CPR chest compressions, the system will then analyze the clean ECG (absent chest compressions) to determine whether a shockable or non-shockable rhythm exists. However, the user might not acknowledge the prompt to stop CPR (e.g., might not see/hear, or may ignore the prompting from the defibrillator) and continue chest compressions. If the user continues chest compressions, despite the prompting to stop chest compressions, the system may continue to apply the continuous analysis advisory that takes into account chest compression artifacts in the ECG. Though, once the user halts chest compressions, the system may immediately or within a short period of time switch the type of ECG analysis from the continuous analysis advisory (with compressions) to a hands-free analysis mode (without compressions), which is able to more accurately confirm whether a shockable or non-shockable rhythm exists.

Figure 4G:
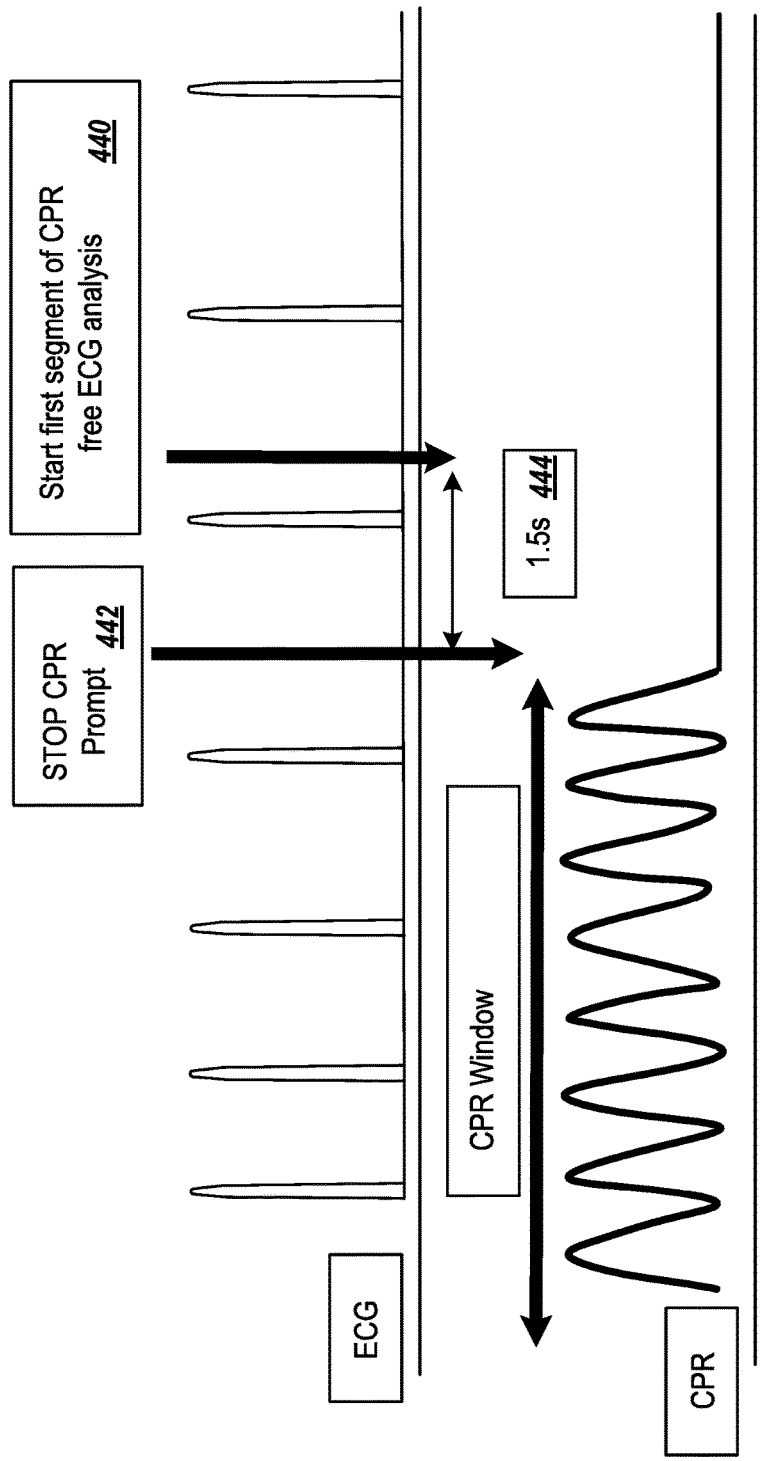

As shown in FIG. 4G, when the defibrillator system determines that chest compressions should cease in favor of analyzing 440 the ECG signal to determine whether a shock should be applied, an instructive prompt 442 is issued for the rescuer to stop CPR and be hands-free from the patient. In various implementations, the system may optionally pause for a short period of time before hands-free ECG analysis. This short pause 444 may be preferable in some cases to ensure that the ECG signal is substantially free of artifact, present or residual, having arisen from the chest compressions. While the example of FIG. 4G shows the short pause time before hands-free ECG analysis to be approximately 1.5 seconds, any appropriate pause time may be employed, such as less than 2 seconds, less than 1.5 seconds, less than 1 second, less than 0.5 seconds, less than 0.2 seconds, less than 0.1 second, etc. In some implementations, while not shown in this figure, upon detection of an interruption in chest compressions, the hands-free ECG analysis advisory may be immediately employed.

Figure 4H:
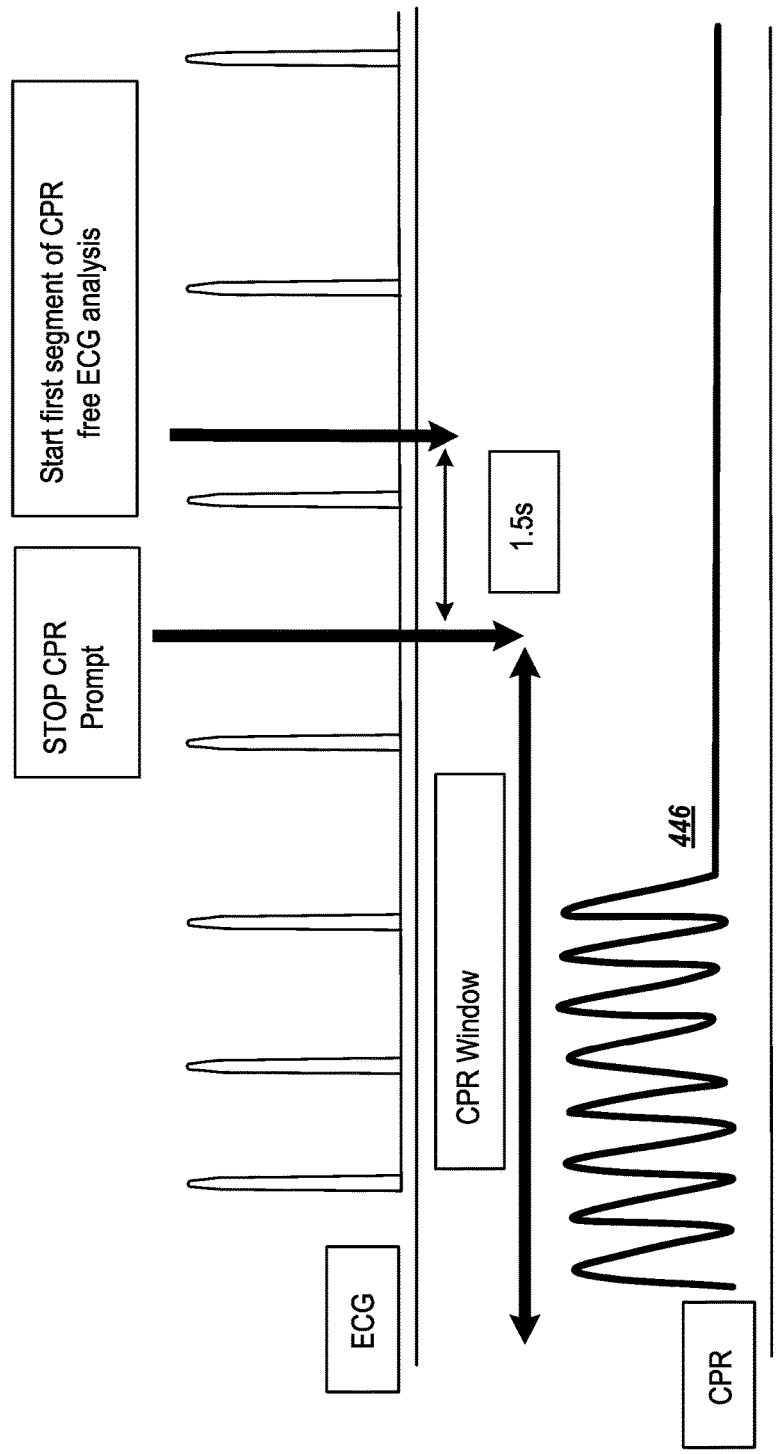

FIG. 4H depicts an implementation where chest compressions are stopped 446 even prior to when the instructive prompt is provided by the system. While it is not advisable to cease chest compressions prematurely, for various reasons, it is common for rescuers to do so. In such a case, while not shown in the figure, the system may prompt the rescuer to continue chest compressions or display an idle timer that shows how long the rescuer has ceased compressions, up until the time when the system determines that chest compressions should be interrupted for hands-free analysis to commence. The implementation of FIG. 4H still pauses for a short period of time after the prompt to stop CPR, however, it can be appreciated that such a pause is not required. For example, when an interruption in chest compressions is detected, the system may automatically and/or immediately begin hands-free ECG analysis advisory without any such pause.

FIG. 4I shows an implementation where chest compressions are continued for a short time 448 (e.g., 1-2 seconds) beyond the time in which the system issues the instructive prompt to stop CPR. In this case, the system tracks the chest compressions up until the time when compressions are ceased, optionally pauses for a short period of time (e.g., approximately 1.5 seconds), and then begins hands-free ECG analysis advisory in accordance with the present disclosure.

Figure 4J:
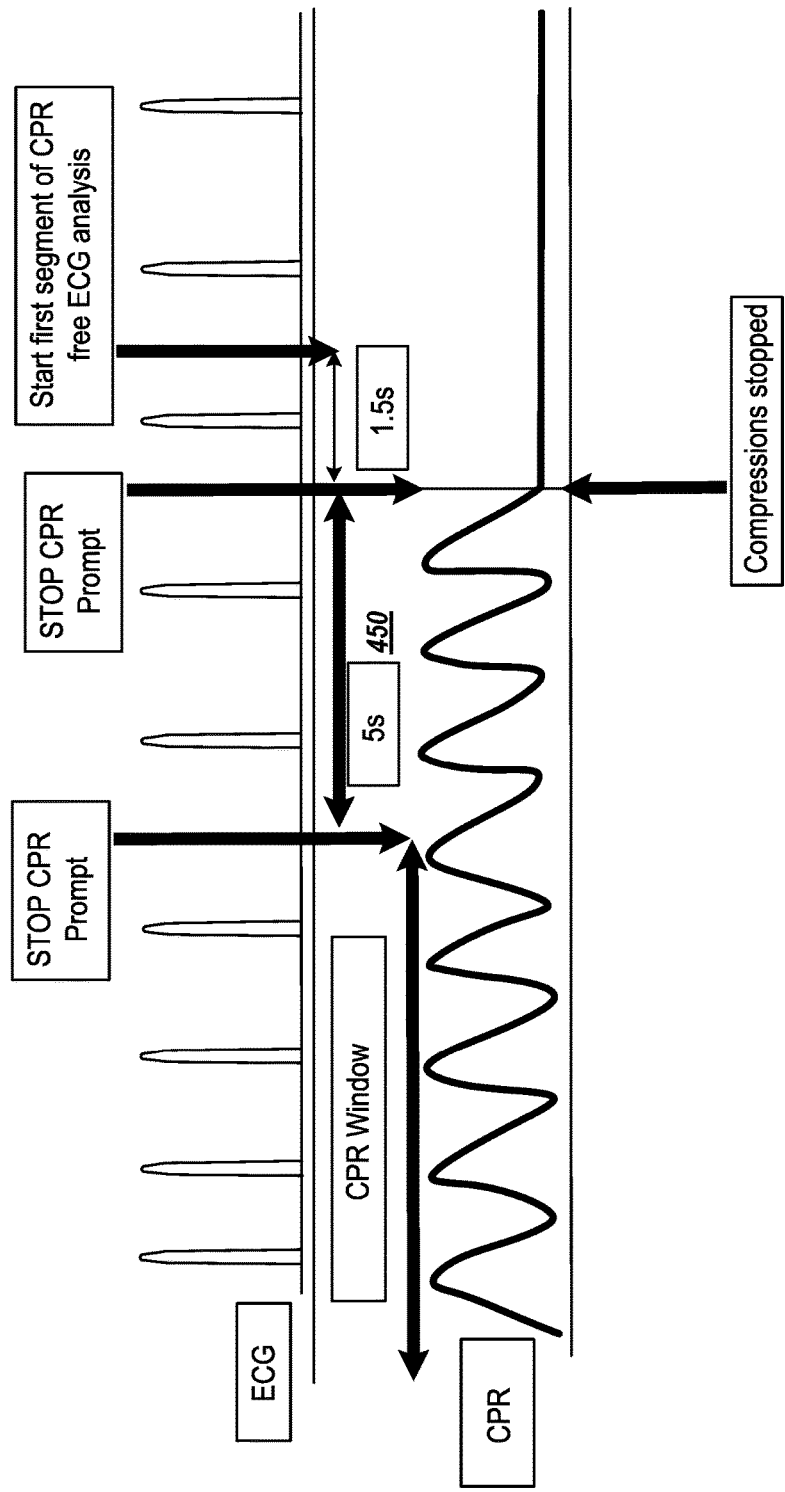

FIG. 4J depicts another implementation of an instance where chest compressions are continued for a longer period 450 than that shown in FIG. 4I. Here, the system continues to track the chest compressions, and after a sufficiently long time period, the system then issues a subsequent instructive prompt reminding the rescuer to stop CPR. It can be appreciated that the subsequent instructive prompt can be provided at any suitable time, which may be predetermined by an appropriate time interval. In this particular case, the system issues the subsequent prompt after approximately 3 seconds which, in some cases, may be similar to an initial time period of ECG analysis. As further shown, when chest compressions are interrupted, the system optionally pauses for a short time (e.g., approximately 1.5 seconds), and then commences hands-free ECG analysis advisory.

Figure 4K:
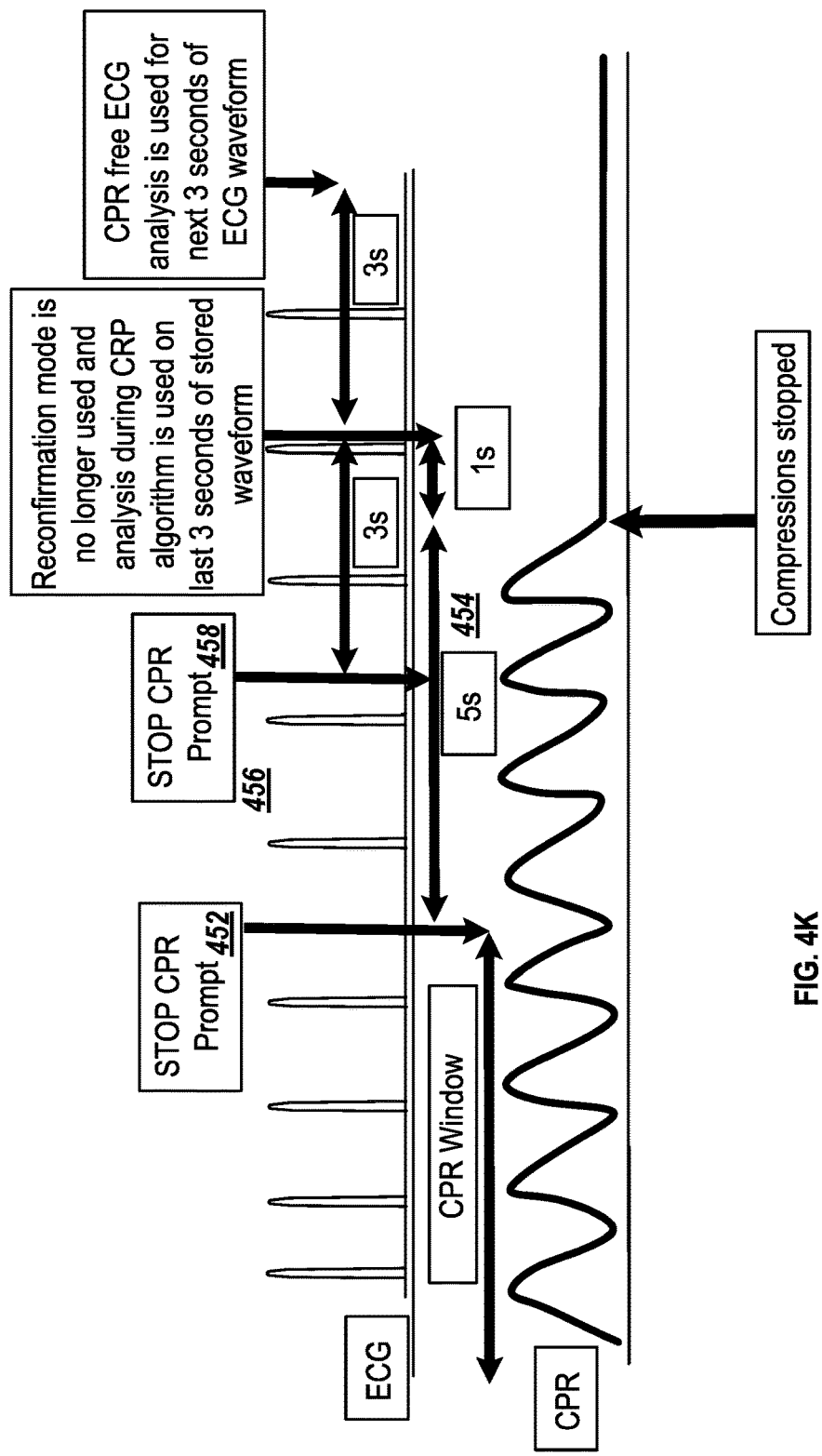

FIG. 4K shows an implementation where chest compressions are continued for an even longer period of time 452. In this example, the system issues the first prompt 454 instructing the user to stop chest compressions, and then after a sufficiently long time interval 456 (e.g., approximately 3 seconds), the system then issues a subsequent instructive prompt 458 reminding the rescuer to stop CPR compressions. However, here, the system continues to sense chest compressions after the subsequent instructive prompt, resulting in further delay in the hands-free CPR analysis advisory. In various implementations, the ECG signal is tracked according to short time segments (e.g., approximately 3 seconds), and once the system identifies an interruption in chest compressions, the hands-free CPR analysis advisory begins at the start of the next time segment. As shown more specifically in FIG. 4K, the system does not detect an interruption in chest compressions until approximately 2 seconds after the most recent instructive prompt to stop CPR compressions. The hands-free CPR analysis advisory then begins after the approximately 1 second that remains in the 3 second interval elapses. Though, for certain implementations, after the subsequent instructive prompt, as soon as an interruption in chest compressions has been determined, the system may immediately begin hands-free CPR analysis advisory, without the optional pause.

Figure 4L:
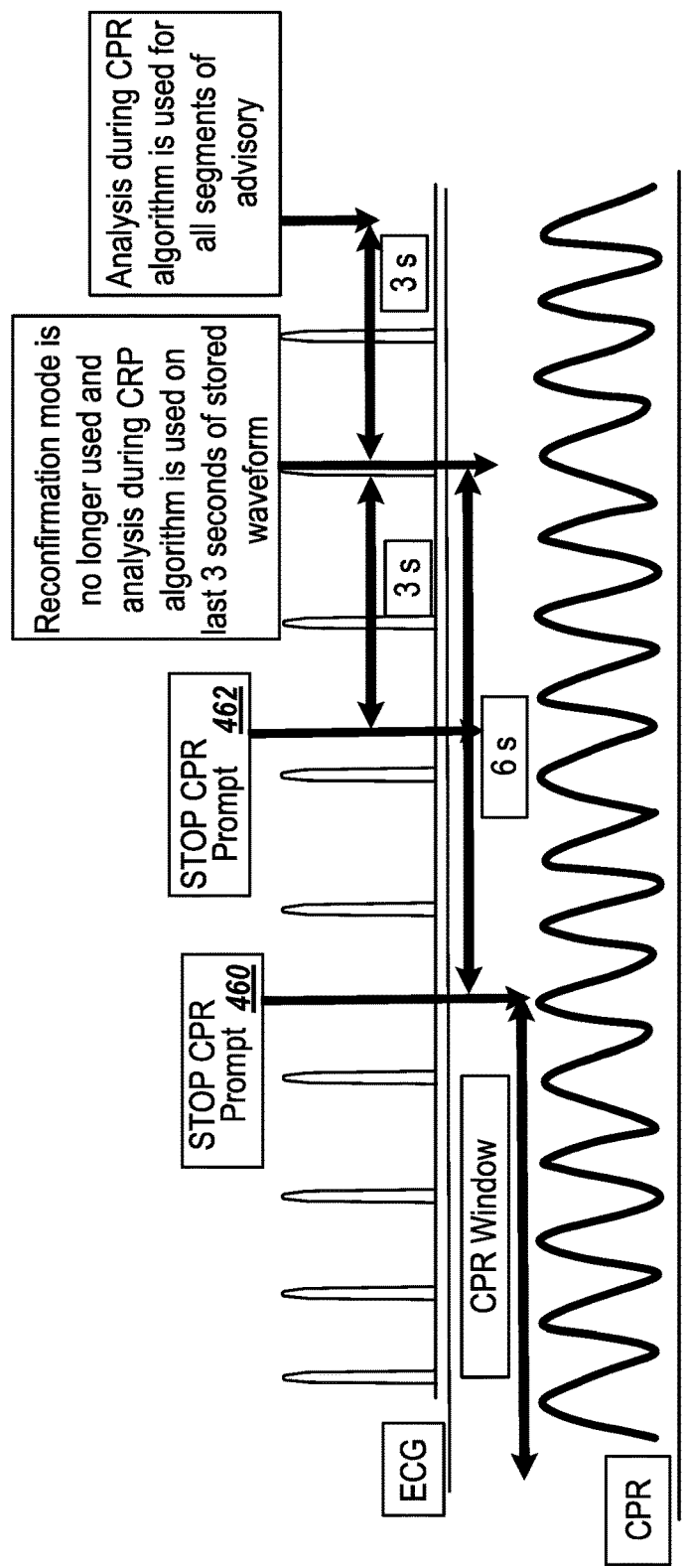

FIG. 4L depicts another illustrative implementation where no interruption in CPR chest compressions is detected, despite multiple instructive prompts 460, 462 to stop chest compressions. In such a case, because chest compressions remain uninterrupted, the hands-free CPR analysis advisory is unable to be used. In this case, the continuous analysis advisory algorithm (which accounts for chest compression artifacts) is applied throughout the time in which chest compressions are administered.

Some examples of parameters that appear in clauses are provided in Table 10.

TABLE 10

| Parameter | Description |
| --- | --- |
| widthvar | Variability in width of QRS complexes |
| Width | Width of QRS complexes |
| qrsv | Variability of R-R interval |
| maxamp | Maximum amplitude of ECG waveform |
| minamp | Absolute minimum amplitude of ECG waveform |
| qrsr | Average R-R interval |
| svtbeats | Number of SVT beats detected in the waveform |

Figure 5A:
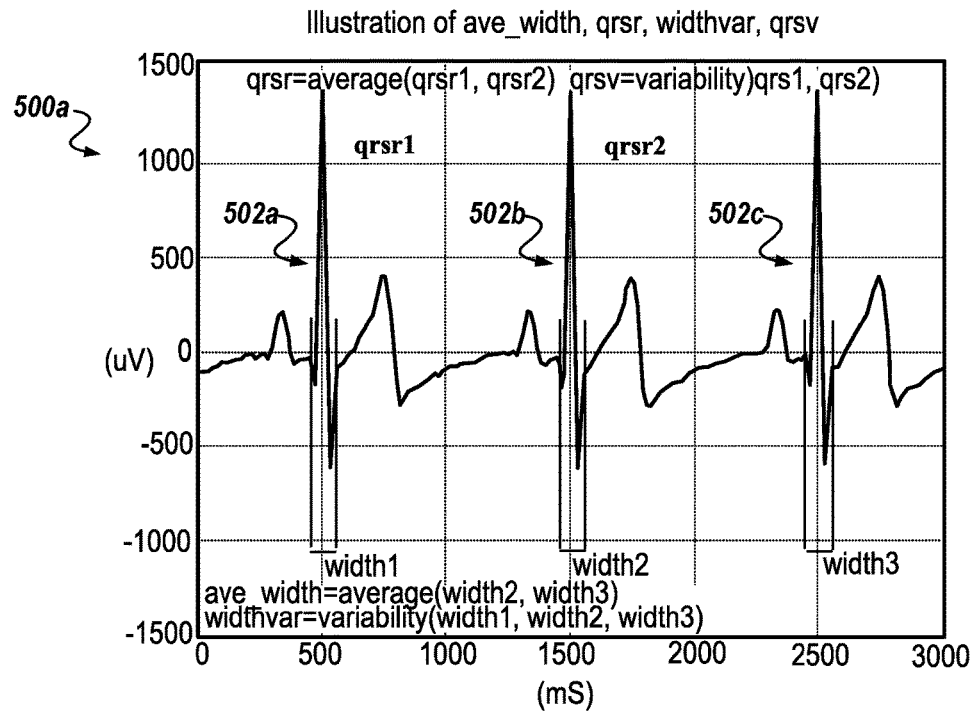
FIGS. 5A-5B show examples of ECG waveforms and their characteristics.
Figure 5B:
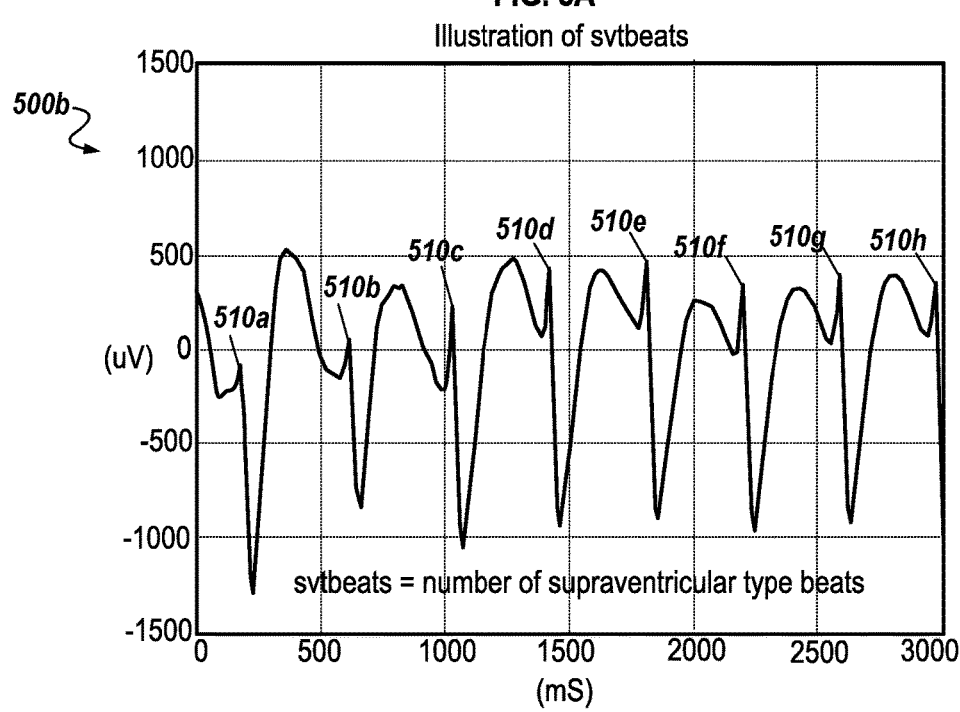

FIGS. 5A-5B show examples of waveforms 500a-500b having characteristics corresponding to some of the parameters listed in Table 10.

FIG. 5A shows an example waveform 500a demonstrating how values for qrsr, widthvar, and qrsv can be calculated. For example, this waveform 500a has three QRS complexes 502a-c having widths (measured in milliseconds) identified by width1, width2, and width3, respectively. Further, the distances (measured from R to R) between the QRS complexes 502a-c is identified by qrsr1 and qrsr2. The parameter qrsr can be calculated by averaging the measurements of the qrsr values, e.g., qrsr1 and qrsr2. The parameter widthvar can be calculated by calculating the variability of the measurements of the widths, e.g., width1, width2, and width3. The parameter qrsv can be calculated by calculating the variability of the qrsr values, e.g., qrsr1 and qrsr2. Variability is determined by sorting the relevant values (e.g., the values for width or the values for qrsr) in order of magnitude, and grouping them in intervals, e.g., intervals of 20 milliseconds. The resulting number of intervals corresponds to variability.

FIG. 5B shows an example waveform 500b demonstrating how a value for svtbeats is calculated. This waveform 500b has eight supraventricular tachycardia type beats 510a-h.

Figure 6A:
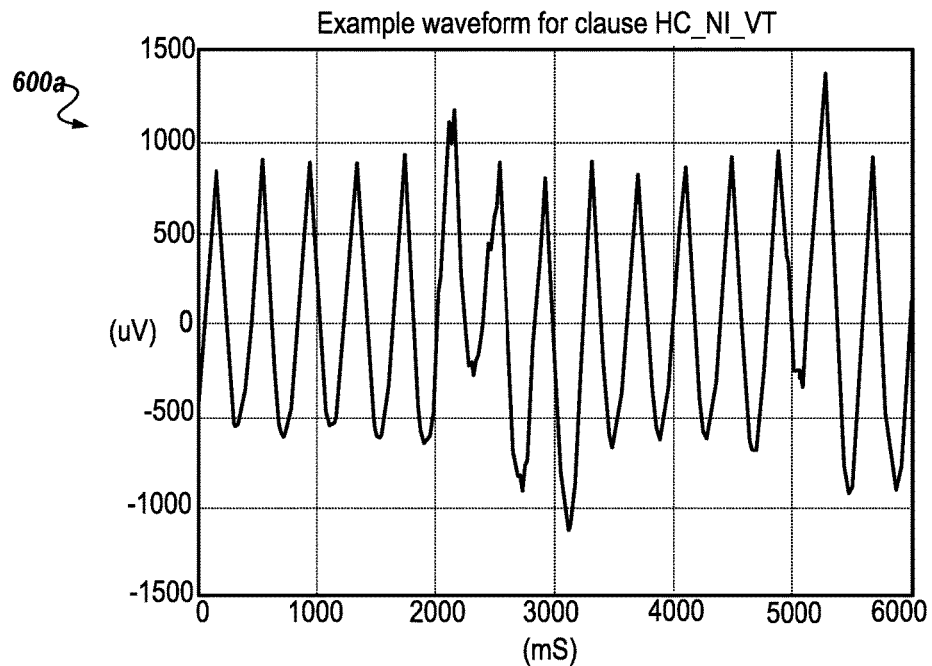
FIGS. 6A-6C show examples of ECG waveforms satisfying respective clauses.

One or more parameters calculated based on ECG data (e.g., parameters provided in Table 10) can be used for defining various high accuracy and normal accuracy clauses used in identifying shockable and non-shockable rhythms in the segment of ECG data. An example waveform 600a of a shockable waveform of ventricular tachycardia is shown in FIG. 6A. The 3-second clause is satisfied (met) when, among other things, the QRS width is greater than 120 ms and there is a limited degree of width variability, which may represent a wide complex rhythm. The clause represents a series of constraints on parameters that correspond to features of an ECG signal. In some cases, wide complex rhythm with R-R interval less than 400 ms can be shockable if the rhythm is VT. However, for some cases, additional checks may be needed to determine the presence of VT with a high accuracy. Checking whether Svtbeats<3 counts rules out that the rhythm represents SVT. Therefore, once all the conditions of the clause are satisfied, the presence of a shockable VT can be identified with a high accuracy.

Figure 6B:
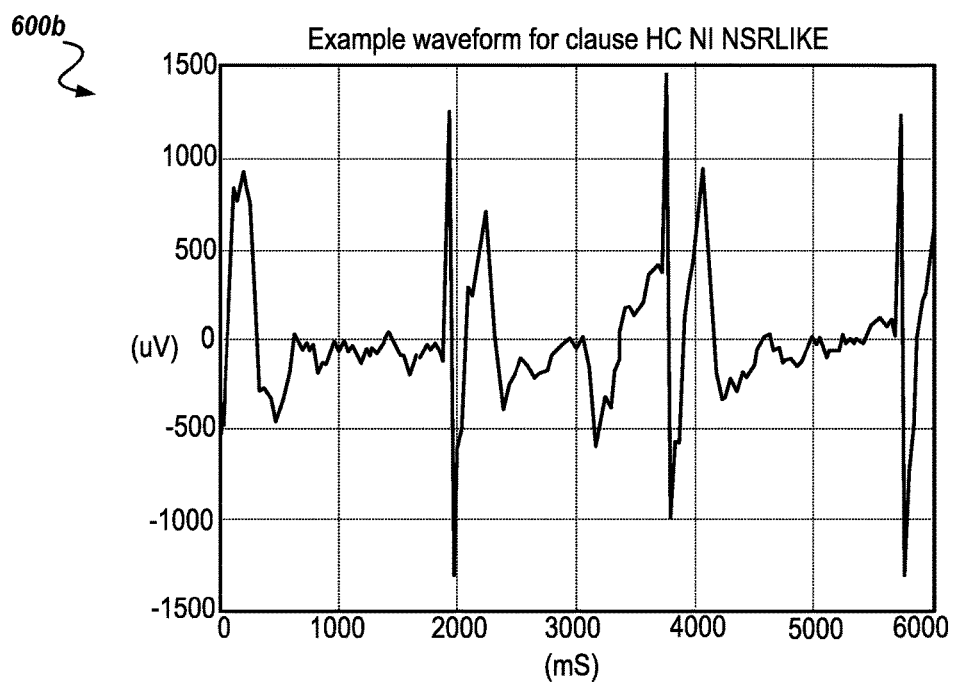

An example non-shockable waveform 600b meeting a 3-second clause is shown in FIG. 6B. This clause is satisfied when the average width of QRS complex is small and there is limited width variability, conditions that may represent a narrow complex rhythm. Because the average amplitude is higher than 300 uV, chances that the QRS detection was erroneous is low. Therefore, with a narrow complex and R-R interval>265 ms, the rhythm corresponding to the underlying ECG data may be identified with high specificity accuracy as non-shockable.

In another implementation of a clause for determining whether an ECG signal is characteristic of a normal sinus rhythm, which returns a non-shockable result, the clause assesses whether the ECG signal has a single clear peak indicative of normal QRS. The clause may identify whether the signal has a maximum slope of greater than a certain threshold and/or whether the signal exhibits substantial periods of flatness where the slope of the analyzed time segment remains below another threshold. For example, a peak characteristic of a normal sinus rhythm may be affirmatively identified if there appears to be a maximum slope of the time segment greater than 50-100 uV (e.g., or greater than 100-150 uV, greater than 150-200 uV, etc.) and/or if the slope of the analyzed time segment remains below 30 uV/ms (e.g., or below 20 microvolts/millisecond, below 10 uV/ms, etc.) for time periods of greater than 50 ms (e.g., or greater than 100 ms, greater than 150 ms, greater than 200 ms, etc.). Examples of such a clause may be evaluated for any suitable time segment, e.g., 0.5 seconds, 1 second, 1.5 seconds, 2 seconds, 2.5 seconds, 3 seconds, amongst others.

In a further implementation of a clause for determining whether an ECG signal is characteristic of asystole type rhythm, which returns a non-shockable result, the ECG signal is evaluated for substantially low amplitudes. Here, the clause may identify whether the magnitude of the maximum or minimum amplitude of the signal is less than a particular threshold. For example, a flatline rhythm may be determined if the magnitude of the maximum amplitude is less than 150 uV (e.g., or less than 100 uV, less than 50 uV, etc.) and/or the magnitude of the minimum amplitude is less than 150 uV (e.g., or less than 100 uV, less than 50 uV, etc.). Examples of this clause may be evaluated for any suitable time segment, e.g., 0.5 seconds, 1 second, 1.5 seconds, 2 seconds, 2.5 seconds, 3 seconds, amongst others.

In an implementation of a clause for determining whether an ECG signal is characteristic of a VF type rhythm, which returns a shockable result, the ECG signal is evaluated for numerous peaks sustained over a sufficient period of time. The clause may be configured to identify whether the maximum slope of the ECG signal is greater than a certain threshold, whether the signal exhibits little flatness and/or whether the waveform crosses the zero point multiple times.

For example, the clause may seek to identify whether the maximum slope of the time segment is greater than 20 uV (e.g., or greater than 50 uV, greater than 100 uV, etc.). The clause may further analyze the signal to determine if the slope of the analyzed time segment remains below 30 uV/milliseconds (e.g., or below 20 microvolts/millisecond, below 10 uV/ms, etc.) for time periods of less than 150 ms (e.g., or less than 100 ms, less than 50 ms, etc.). In addition, the clause may analyze the signal to determine whether the waveform crosses the zero point greater than 5 times (e.g., or greater than 10 times, greater than 20 times, greater than 30 times, etc.). Examples of such a clause may be evaluated for an appropriate period of time, e.g., 1 second, 1.5 seconds, 2 seconds, 2.5 seconds, 3 seconds, etc.

In an implementation of another clause evaluating an ECG signal for whether it is a VT type rhythm, the clause determines whether the ECG signal exhibits a high frequency with wide complexes. In particular, the clause may assess the signal to identify whether the average peak to peak interval of the waveform is less than a particular threshold, whether the average width of the QRS complex(es) is greater than a threshold and/or whether the overall width variation of the QRS complex(es) is relatively regular. For example, the clause may assess whether the average peak to peak interval of the ECG signal for the time segment of analysis is less than 500 ms (e.g., or less than 400 ms, less than 350 ms, less than 300 ms, less than 250 ms, etc.). The clause may also determine whether the average width of the QRS complex(es) is greater than 50 ms (e.g., or greater than 100 ms, greater than 150 ms, greater than 200 ms, etc.), as well as evaluate whether the variability of the width of the QRS complex(es) is substantially regular.

Figure 6C:
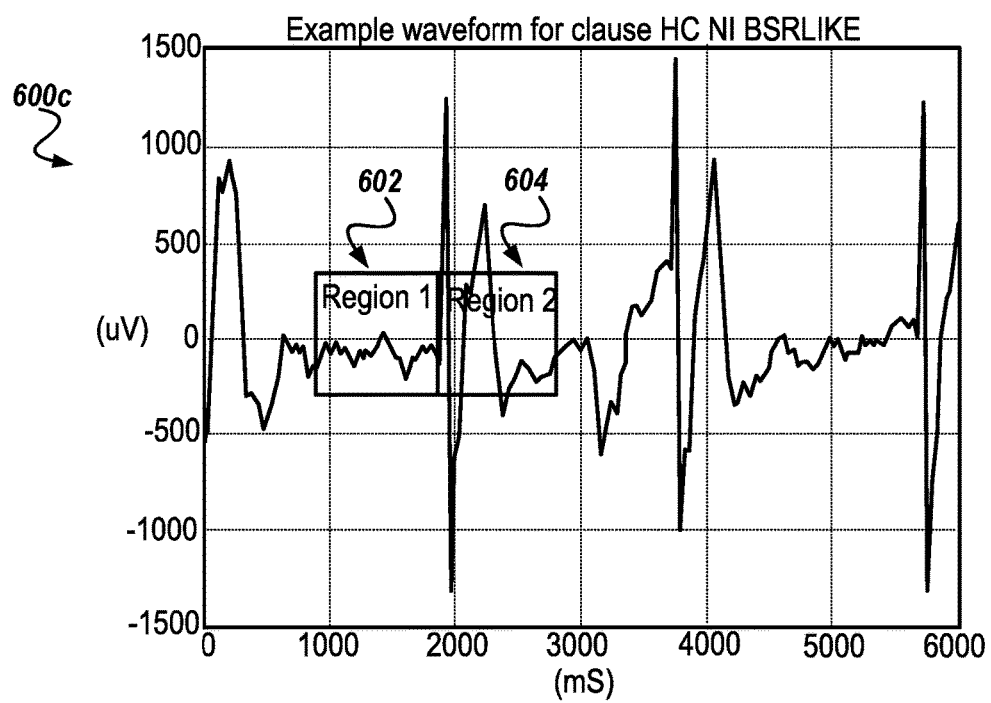

In another implementation of a clause for determining whether an ECG signal is characteristic of a VT type rhythm, which returns a shockable result, the ECG is assessed for a fast heart rate with wide QRS complexes for a period of 4-8 seconds (e.g., approximately 6 seconds). The clause may be configured to identify whether the heart rate is above a certain threshold (e.g., greater than 120 bpm, greater than 130 bpm, greater than 140 bpm, greater than 150 bpm, greater than 160 bpm, etc.), whether the interval between peaks is less than a threshold (e.g., less than 600 ms, less than 500 ms, less than 400 ms, less than 300 ms, etc.), whether the width of the QRS complexes is greater than a threshold (e.g., greater than 120 ms, greater than 130 ms, greater than 140 ms, greater than 150 ms, greater than 160 ms, etc.), whether the overall width variation of the QRS complex(es) is relatively regular and/or whether the signal exhibits little flatness (e.g., ECG during analyzed time segment remains below 50 uV/ms for time periods of greater than 100 ms). As also discussed herein, systems and methods of fast ECG analysis described herein may involve incrementally extending the time period of ECG analysis if it is indeterminate whether the ECG rhythm is shockable or non-shockable. For example, referring to FIG. 6C, the ECG analysis may commence at a first region 602 of the ECG signal 600c, which is shown to last for approximately 1 second. Though, in this example, the ECG signal may not provide sufficient information for the clauses associated with the 1 second time segment to make a final determination of shockable or non-shockable. Accordingly, the time segment of ECG analysis may be incrementally extended so as to gather more information to make a final decision. As shown in FIG. 6C in a second region 604, the variable-length time segment is extended for another second. In the extended window of analysis, a QRS waveform characteristic of a normal sinus is identified, resulting in the identification of a non-shockable ECG rhythm.

As noted above, Table 2 includes a number of exemplary clauses which may be used as 3-second clauses for an initial rule set. As an example, for an initial time period (e.g., 3 seconds) of ECG analysis, if any of the clauses labeled as high accuracy are met, then a decision of whether the rhythm is shockable or non-shockable is made, without further need for analysis. As discussed herein, it should be understood that the initial time period can span any appropriate period of time. For instance, exemplary clauses similar to those provided in Tables 1 and 3 for other time segments of analysis may be applied.

Table 3 includes a number of exemplary clauses which may be used as 6-second clauses for an adjusted rule set. Continuing the above example, if none of the high accuracy clauses are met, then the time period of analysis proceeds further, and an adjusted rule set is applied. Hence, the initial time period may be extended to an adjusted time period (e.g., 6 seconds) of ECG analysis. For that adjusted time period, as discussed for certain implementations, the extended duration segment may be further sub-divided and the new clause or rule set may employ such techniques, known to those skilled in the art, as the voting model. In such a case, the new adjusted, longer duration clauses may be separately applied to multiple time segments (e.g., multiple 3 second time segments, adding up to 6-9 seconds or 6-12 seconds of ECG analysis) over the span of the adjusted time period. For each of the time segments, a vote of shockable or non-shockable is returned and a decision of whether to shock or not shock is based on the results of the vote.

In various implementations, input from sensors other than those used to sense the electrical activity of the heart may be employed by the analysis algorithm to provide information that leads to a determination of whether the patient is in a shockable or non-shockable state sooner than would otherwise be the case without the additional information. For example, it has been shown that a motion sensor (e.g., accelerometer) may be used to measure heart wall motion, and may further provide an indication of whether or not the patient's heart has achieved a normal sinus rhythm. This concept is described in International Patent Application No. PCT/US16/37081, entitled "Detection of Myocardial Contractions Indicative of Perfusion," filed on Jun. 10, 2016, and is incorporated by reference herein in its entirety. If additional sensor input provides evidence that the heart is beating regularly mechanically, then the analysis algorithm may more quickly come to a conclusion that a defibrillation shock should not be applied to the patient. Alternatively, if the additional sensor shows that the heart is beating irregularly, then the analysis algorithm may require further information to make a final determination as to whether the patient should be defibrillated.

It can be appreciated that the teachings of the present disclosure can be generally applied to external medical monitoring and/or treatment devices (e.g., devices that are not completely implanted within the patient's body). That is, algorithms described herein for analyzing a patient's ECG to quickly determine whether it is appropriate to apply a defibrillating shock to the heart are applicable to external medical monitoring and/or treatment devices. External medical devices can include, for example, ambulatory medical devices that are capable of and designed for moving with the patient as the patient goes about his or her daily routine. An example ambulatory medical device is a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device is capable of continuous (e.g., substantially or nearly continuous) use by the patient. In some implementations, the continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provide specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. Such a patient monitoring device may be equipped with algorithms described herein for determining whether a patient is in need of electrotherapy such as defibrillation. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's electrocardiogram (ECG) information, and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrioventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters.

Example Wearable Medical Devices

Figure 7:
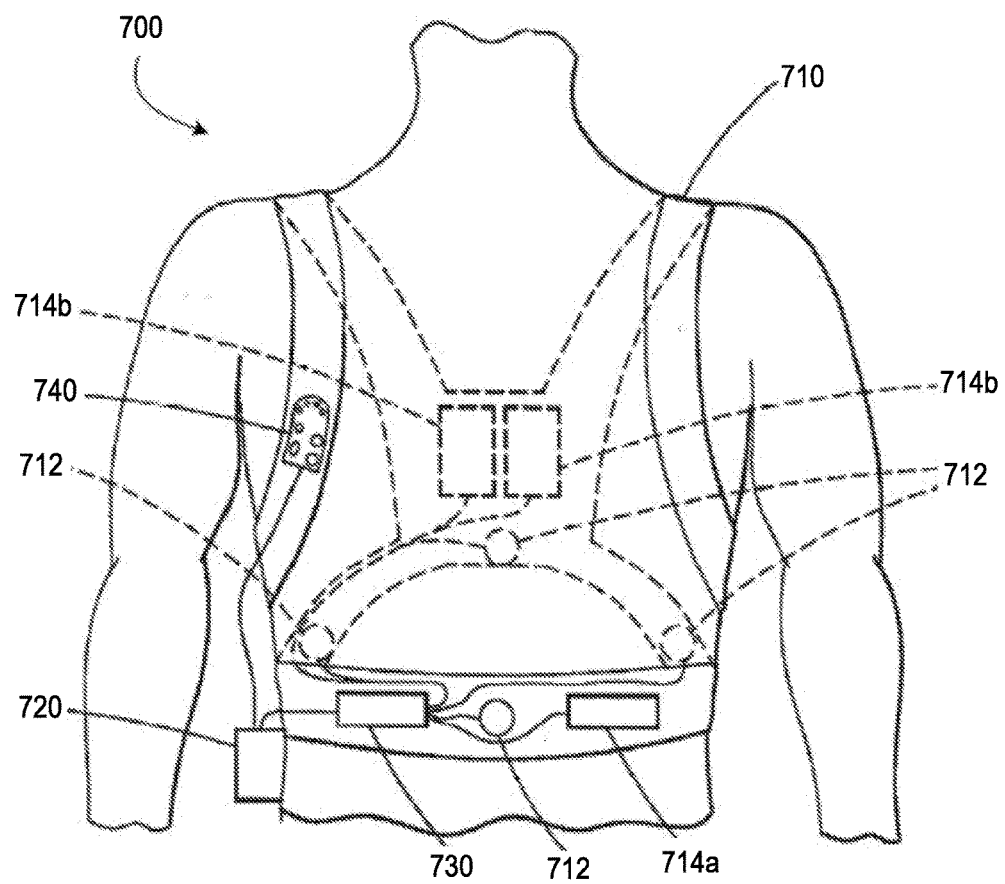
FIG. 7 shows an example of a medical device that may be used in implementations described herein.

FIG. 7 illustrates an example medical device 700 that is external, ambulatory, and wearable by a patient 702, and configured to implement one or more configurations described herein. For example, the medical device 700 can be a non-invasive medical device configured to be located substantially external to the patient. Such a medical device 700 can be, for example, an ambulatory medical device that is capable of and designed for moving with the patient as the patient goes about his or her daily routine. For example, the medical device 700 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 700 can include one or more of the following: a garment 710, one or more sensing electrodes 712 (e.g., ECG electrodes), one or more therapy electrodes 714, a medical device controller 720, a connection pod 730, a patient interface pod 740, a belt 750, or any combination of these. In some examples, at least some of the components of the medical device 700 can be configured to be affixed to the garment 710 (or in some examples, permanently integrated into the garment 710), which can be worn about the patient's torso.

The medical device controller 720 can be operatively coupled to the sensing electrodes 712, which can be affixed to the garment 710, e.g., assembled into the garment 710 or removably attached to the garment, e.g., using hook and loop fasteners. In some implementations, the sensing electrodes 712 can be permanently integrated into the garment 710. The medical device controller 720 can be operatively coupled to the therapy electrodes 714. For example, the therapy electrodes 714 can also be assembled into the garment 710, or, in some implementations, the therapy electrodes 714 can be permanently integrated into the garment 710.

Component configurations other than those shown in FIG. 7 are possible. For example, the sensing electrodes 712 can be configured to be attached at various positions about the body of the patient 702. The sensing electrodes 712 can be operatively coupled to the medical device controller 720 through the connection pod 730. In some implementations, the sensing electrodes 712 can be adhesively attached to the patient 702. In some implementations, the sensing electrodes 712 and therapy electrodes 714 can be included on a single integrated patch and adhesively applied to the patient's body.

The sensing electrodes 712 can be configured to detect one or more cardiac signals. Examples of such signals include ECG signals, chest wall motion, and/or other sensed cardiac physiological signals from the patient. The sensing electrodes 712 can also be configured to detect other types of patient physiological parameters, such as tissue fluid levels, lung sounds, respiration sounds, patient movement, etc. Example sensing electrodes 712 include a metal electrode with an oxide coating such as tantalum pentoxide electrodes, as described in, for example, U.S. Pat. No. 6,253,099, issued Jun. 26, 2001, entitled "Cardiac Monitoring Electrode Apparatus and Method," the content of which is incorporate herein by reference.

In some examples, the therapy electrodes 714 can also be configured to include sensors configured to detect ECG signals as well as other physiological signals of the patient. The connection pod 730 can, in some examples, include a signal processor configured to amplify, filter, and digitize these cardiac signals prior to transmitting the cardiac signals to the medical device controller 720. One or more therapy electrodes 714 can be configured to deliver one or more therapeutic defibrillating shocks to the body of the patient 702 when the medical device 700 determines that such treatment is warranted based on the signals detected by the sensing electrodes 712 and processed by the medical device controller 720. Example therapy electrodes 714 can include conductive metal electrodes such as stainless steel electrodes that include, in certain implementations, one or more conductive gel deployment devices configured to deliver conductive gel to the metal electrode prior to delivery of a therapeutic shock. In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 714 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

WMD/WCD Controller Description

Figure 8:
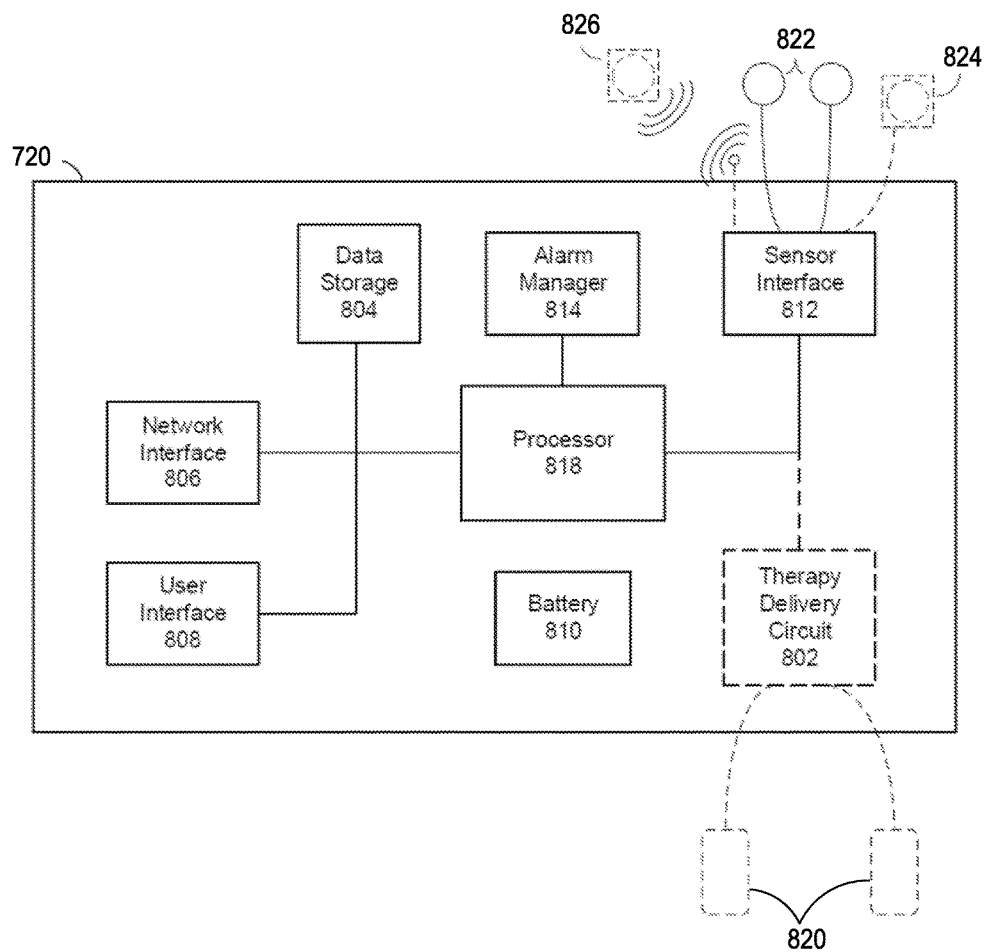
FIG. 8 shows another example of a medical device that may be used in implementations described herein.

FIG. 8 illustrates a sample component-level view of the medical device controller 720. As shown in FIG. 8, the medical device controller 720 can include a therapy delivery circuit 802, a data storage 804, a network interface 806, a user interface 808, at least one battery 810, a sensor interface 812, an alarm manager 814, and least one processor 818. A patient monitoring medical device can include a medical device controller 720 that includes like components as those described above, but does not include the therapy delivery circuit 802 (shown in dotted lines).

The therapy delivery circuit 802 can be coupled to one or more electrodes 820 configured to provide therapy to the patient (e.g., therapy electrodes 714a-b as described above in connection with FIG. 7). For example, the therapy delivery circuit 802 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 818) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 microfarads can be used. The capacitors can have a surge rating between 350 and 500 volts and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 802 can be configured to perform the switching and pulse delivery operations, e.g., under control of the processor 818. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 804 can include one or more of non-transitory computer readable media, such as flash memory, solid state memory, magnetic memory, optical memory, cache memory, combinations thereof, and others. The data storage 804 can be configured to store executable instructions and data used for operation of the medical device controller 720. In certain implementations, the data storage can include executable instructions that, when executed, are configured to cause the processor 818 to perform one or more functions.

In some examples, the network interface 806 can facilitate the communication of information between the medical device controller 720 and one or more other devices or entities over a communications network. For example, where the medical device controller 720 is included in an ambulatory medical device (such as medical device 700), the network interface 806 can be configured to communicate with a remote computing device such as a remote server or other similar computing device.

In certain implementations, the user interface 808 can include one or more physical interface devices such as input devices, output devices, and combination input/output devices and a software stack configured to drive operation of the devices. These user interface elements may render visual, audio, and/or tactile content, including content relating to location-specific processing. Thus the user interface 808 may receive input or provide output, thereby enabling a user to interact with the medical device controller 720.

The medical device controller 720 can also include at least one battery 810 configured to provide power to one or more components integrated in the medical device controller 720. The battery 810 can include a rechargeable multi-cell battery pack. In one example implementation, the battery 810 can include three or more 2200 mAh lithium ion cells that provides electrical power to the other device components within the medical device controller 720. For example, the battery 810 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 720.

The sensor interface 812 can be coupled to one or more sensors configured to monitor one or more physiological parameters of the patient. As shown, the sensors may be coupled to the medical device controller 720 via a wired or wireless connection. The sensors can include one or more electrocardiogram (ECG) electrodes 822 (e.g., similar to sensing electrodes 712 as described above in connection with FIG. 7), other physiological or motion sensors 824, and tissue fluid monitors 826 (e.g., based on ultra-wide band radiofrequency devices).

The ECG electrodes 822 can monitor a patient's ECG information. For example, the ECG electrodes 822 can be conductive and/or capacitive electrodes configured to measure changes in a patient's electrophysiology to measure the patient's ECG information. The ECG electrodes 822 can transmit information descriptive of the ECG signals to the sensor interface 812 for subsequent analysis using algorithms such as those described above. Such analysis may be performed by the processor 818, or another processor associated with the system.

The tissue fluid monitors 826 can use radio frequency (RF) based techniques to assess fluid levels and accumulation in a patient's body tissue. For example, the tissue fluid monitors 826 can be configured to measure fluid content in the lungs, typically for diagnosis and follow-up of pulmonary edema or lung congestion in heart failure patients. The tissue fluid monitors 826 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 826 can transmit information descriptive of the tissue fluid levels to the sensor interface 812 for subsequent analysis.

The sensor interface 812 can be coupled to any one or combination of sensing electrodes/other sensors to receive other patient data indicative of patient parameters. Once data from the sensors has been received by the sensor interface 812, the data can be directed by the processor 818 to an appropriate component within the medical device controller 720. For example, if heart data is collected by a sensor 824 and transmitted to the sensor interface 812, the sensor interface 812 can transmit the data to the processor 818 which, in turn, relays the data to a cardiac event detector. The cardiac event data can also be stored on the data storage 804.

In certain implementations, the alarm manager 814 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 814 can be implemented using hardware or a combination of hardware and software. For instance, in some examples, the alarm manager 814 can be implemented as a software component that is stored within the data storage 804 and executed by the processor 818. In this example, the instructions included in the alarm manager 814 can cause the processor 818 to configure alarm profiles and notify intended recipients using the alarm profiles. In other examples, alarm manager 814 can be an application-specific integrated circuit (ASIC) that is coupled to the processor 818 and configured to manage alarm profiles and notify intended recipients using alarms specified within the alarm profiles. Thus, examples of alarm manager 814 are not limited to a particular hardware or software implementation.

In some implementations, the processor 818 includes one or more processors (or one or more processor cores) that each are configured to perform a series of instructions that result in manipulated data and/or control the operation of the other components of the medical device controller 720. In some implementations, when executing a specific process (e.g., cardiac monitoring), the processor 818 can be configured to make specific logic-based determinations based on input data received, and be further configured to provide one or more outputs that can be used to control or otherwise inform subsequent processing to be carried out by the processor 818 and/or other processors or circuitry with which processor 818 is communicatively coupled. Thus, the processor 818 reacts to specific input stimulus in a specific way and generates a corresponding output based on that input stimulus. In some example cases, the processor 818 can proceed through a sequence of logical transitions in which various internal register states and/or other bit cell states internal or external to the processor 818 may be set to logic high or logic low. As referred to herein, the processor 818 can be configured to execute a function where software is stored in a data store coupled to the processor 818, the software being configured to cause the processor 818 to proceed through a sequence of various logic decisions that result in the function being executed. The various components that are described herein as being executable by the processor 818 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

Figure 9:
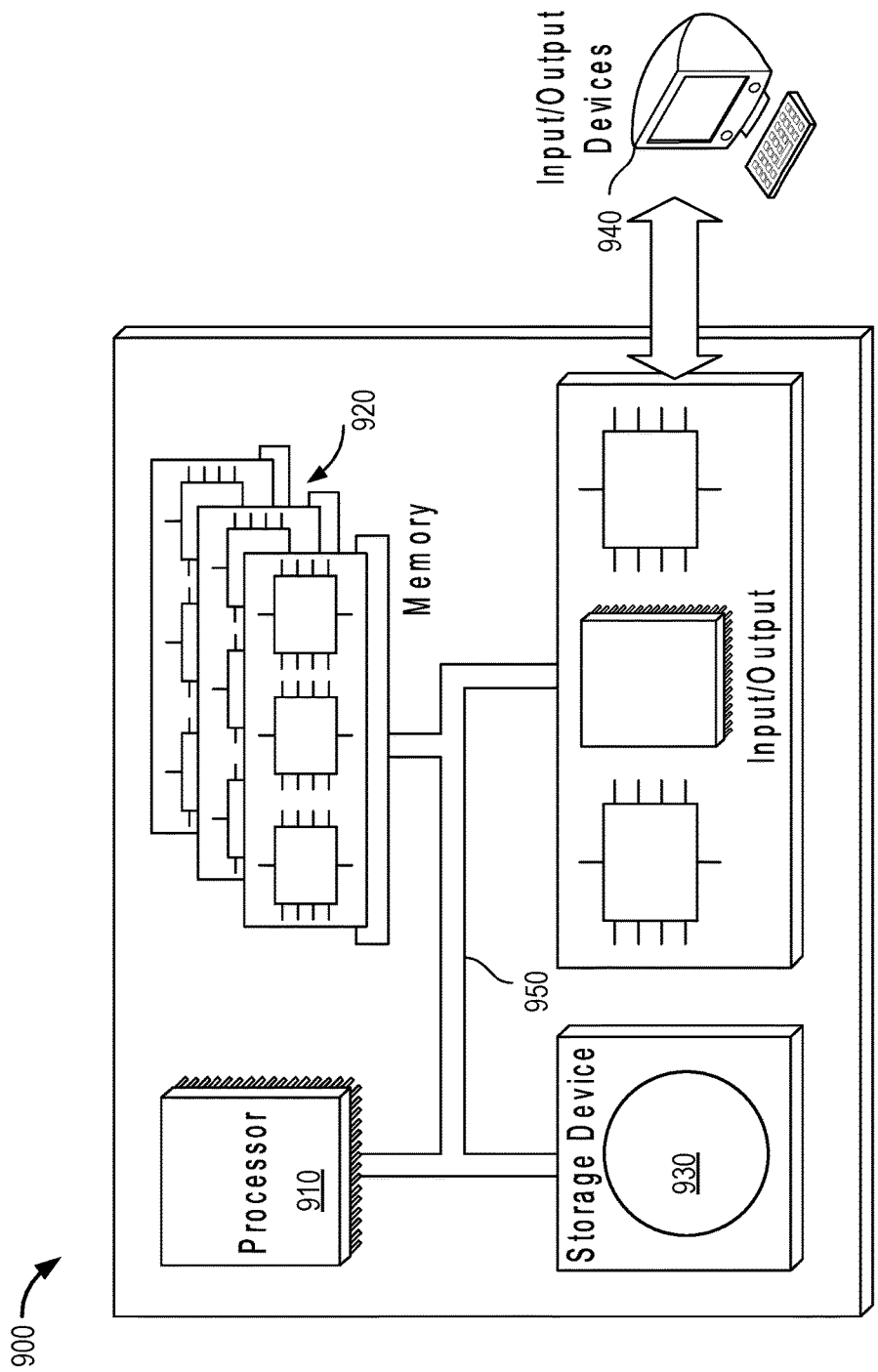
FIG. 9 shows an example of a computing system, which may be used with the techniques described here.

The particular techniques described here may be assisted by the use of a computer-implemented medical device, such as a defibrillator that includes computing capability. Such a defibrillator or other device can include a computer system 900 as shown in FIG. 9, and may communicate with and/or incorporate a computer system 900 in performing the operations discussed above. For example, one or more of the ECG analyzer module 905, TTI module 908, CPR feedback module 910, PTI module 912, and logic module 918 can include at least a portion of the computing system 900. The system 900 may be implemented in various forms of digital computers, including computerized defibrillators laptops, personal digital assistants, tablets, and other appropriate computers. Additionally, the system can include portable storage media, such as Universal Serial Bus (USB) flash drives. For example, the USB flash drives may store operating systems and other applications. The USB flash drives can include input/output components, such as a wireless transmitter or USB connector that may be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor may be designed using any of a number of architectures. For example, the processor 910 may be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 900. In one implementation, the storage device 930 is a computer-readable medium. In various different implementations, the storage device 930 may be a floppy disk device, a hard disk device, an optical disk device, or a tape device.

The input/output device 940 provides input/output operations for the system 900. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier (e.g., in a machine-readable storage device for execution by a programmable processor) and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks (such as internal hard disks and removable disks), magneto-optical disks, and optical disks. Storage devices suitable for tangibly embodying computer program instructions and data include all forms of non-volatile memory, including by way of example semiconductor memory devices (such as EPROM, EEPROM) and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user, a keyboard, and a pointing device such as a mouse or a trackball by which the user can provide input to the computer.

The features can be implemented in a computer system that includes a back-end component (such as a data server) or a middleware component (such as an application server or an Internet server), or a front-end component (such as a client computer having a graphical user interface or an Internet browser), or any combination of them. The components of the system can be connected by any form or medium of digital data communication, such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Although the subject matter contained herein has been described in detail for the purpose of illustration, it is to be understood that such detail is solely for that purpose and that the present disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

Other implementations other than those described may be employed, and may be encompassed by the following claims.

What is claimed is:

1. A defibrillator comprising:
   one or more capacitors for delivering a defibrillating shock to a patient;
   one or more electronic ports for receiving signals from at least one sensor for obtaining indications of an electrocardiogram (ECG) for the patient;
   a patient treatment circuit executable on one or more processing devices configured for:
      receiving data representing an ECG signal,
      processing a variable-length time segment of the ECG signal comprising an initial time period, wherein the processing comprises
         identifying one or more features of the variable-length time segment based on an initial rule set corresponding to the initial time period, for determining whether an ECG rhythm represented by the ECG signal is shockable or non-shockable,
         based on the initial rule set, determining whether the ECG rhythm represented by the ECG signal is shockable or non-shockable or whether to extend the variable-length time segment for further analysis, extending the initial time period of the variable-length time segment by one or more additional time periods,
identifying one or more features of the variable-length time segment based on an adjusted rule set corresponding to an adjusted time period, for updating the determination of whether the ECG rhythm is shockable or non-shockable; and
a delivery circuit configured to deliver a treatment to the patient based on the determination.

2. The defibrillator of claim 1 wherein the initial time period is between 0.1 second and approximately 3 seconds.

3. The defibrillator of claim 1 wherein extending the variable-length time segment comprises extending the variable-length time segment by an additional time period of between 0.1 second and approximately 3 seconds.

4. The defibrillator of claim 1 wherein the determination of whether the ECG rhythm is shockable or non-shockable is made after processing the variable-length time segment of the ECG signal for less than 6 seconds.

5. The defibrillator of claim 1 wherein the length of the time segment being processed varies based on identity of the one or more features being used to make the determination of whether the ECG rhythm is shockable or non-shockable.

6. The defibrillator of claim 1 wherein the processing comprises identifying whether an interruption in chest compressions has occurred, and analyzing the variable-length time segment of the ECG signal during the chest compression interruption according to the initial rule set.

7. The defibrillator of claim 6 wherein identifying whether the interruption in chest compressions has occurred comprises processing signals produced from at least one of an ECG electrode and a motion sensor.

8. The defibrillator of claim 1 wherein the initial rule set includes one or more clauses representing constraints on one or more features of the ECG signal, each of the one or more features of the ECG signal representing a characteristic of a waveform of the ECG signal within the variable-length time segment.

9. The defibrillator of claim 1 wherein the processing comprises analyzing the variable-length time segment of the ECG signal during chest compressions according to a continuous analysis rule set prior to the initial time period.

10. The defibrillator of claim 9 wherein the analyzing the variable-length time segment of the ECG signal during chest compressions according to the continuous analysis rule set occurs prior to identifying whether an interruption in chest compressions has occurred.

11. The defibrillator of claim 10 wherein determining whether the ECG rhythm represented by the ECG signal is shockable or non-shockable comprises comparing analysis of the ECG signal during the chest compression interruption according to the initial rule set with analysis of the ECG signal during chest compressions according to the continuous analysis rule set.

12. The defibrillator of claim 1 wherein the one or more processing devices are configured for storing the ECG data in a buffer configured to hold data representing the variable-length time segment of the ECG signal.

13. The defibrillator of claim 1 wherein the one or more processing devices are configured for causing the one or more capacitors to begin a charging sequence if the ECG rhythm is determined to be shockable.

14. The defibrillator of claim 1, comprising an output circuit that is configured to present a user interface configured for providing feedback indicating if the ECG rhythm is shockable or non-shockable.

15. The defibrillator of claim 1, wherein the initial rule set includes at least one high accuracy clause and the adjusted rule set includes at least one clause different from the at least one high accuracy clause.

16. The defibrillator of claim 1, wherein the adjusted rule set employs a voting scheme that divides the variable-length time segment into a plurality of voting segments, each voting segment providing a voting determination of whether the ECG rhythm represented by the ECG signal during the respective voting segment is shockable or non-shockable.

17. The defibrillator of claim 16, wherein the determination of whether the ECG rhythm is shockable or non-shockable is based on the voting determination of the plurality of voting segments.

18. The defibrillator of claim 1, wherein the defibrillator comprises a wearable ambulatory medical device including a garment configured to:
be worn about a torso of the patient for an extended period of time,
support one or more components of the defibrillator, and
receive at least one ECG sensing electrode for sensing the ECG signal of the patient and at least one therapy electrode for providing a therapeutic shock to the patient.

19. The defibrillator of claim 1, wherein the defibrillator is configured to substantially continuously monitor the ECG signal of the patient and provide a therapeutic shock on detecting a shockable ECG rhythm.

20. The defibrillator of claim 1, wherein extending the variable-length time segment comprises extending the variable-length time segment by an additional time period of between 0.1 and 2 seconds.

21. A defibrillator comprising:
one or more capacitors for delivering a defibrillating shock to a patient;
one or more electronic ports for receiving signals from at least one sensor for obtaining indications of an electrocardiogram (ECG) for the patient;
a patient treatment circuit executable on one or more processing devices configured for:
receiving data representing an ECG signal,
processing a variable-length time segment of the ECG signal comprising an initial time period of between 0.1 second and approximately 3 seconds, the initial time period, wherein the processing comprises
identifying whether an interruption in chest compressions has occurred,
analyzing the variable-length time segment of the ECG signal during the chest compression interruption according to an initial rule set based on the initial time period, for determining whether an ECG rhythm represented by the ECG signal is shockable or non-shockable,
based on the initial rule set, determining whether the ECG rhythm represented by the ECG signal is shockable or non-shockable or whether to extend the variable-length time segment for further analysis,
generating an output based on the determination of whether the ECG rhythm represented by the ECG signal is shockable or non-shockable; and
a delivery circuit configured to deliver a treatment to the patient based on the determination.

22. The defibrillator of claim 21 wherein identifying whether the interruption in chest compressions has occurred comprises processing signals produced from at least one of an ECG electrode and a motion sensor.

23. The defibrillator of claim 21 wherein the initial rule set includes one or more clauses representing constraints on one or more features of the ECG signal, each of the one or more features of the ECG signal representing a characteristic of a waveform of the ECG signal within the variable-length time segment.

24. The defibrillator of claim 23 wherein the patient treatment circuit is configured for generating a prompt instructing a user to stop CPR chest compressions, and wherein identifying the chest compression interruption occurs after generating the prompt instructing the user to stop CPR chest compressions.

25. The defibrillator of claim 24, wherein the patient treatment circuit is configured for generating a subsequent prompt instructing a user to stop CPR chest compressions based on whether the chest compression interruption has been identified.

26. The defibrillator of claim 21 wherein analyzing the variable-length time segment of the ECG signal occurs approximately 1.5 seconds or less after identifying the chest compression interruption.

27. The defibrillator of claim 21 wherein the processing comprises analyzing the variable-length time segment of the ECG signal during chest compressions according to a continuous analysis rule set prior to the initial time period, and prior to identifying whether the interruption in chest compressions has occurred.

28. The defibrillator of claim 27 wherein determining whether the ECG rhythm represented by the ECG signal is shockable or non-shockable comprises comparing analysis of the ECG signal during the chest compression interruption according to the initial rule set with analysis of the ECG signal during chest compressions according to the continuous analysis rule set.

29. The defibrillator of claim 21 comprising extending the initial time period of the variable-length time segment by one or more additional time periods, and analyzing the variable-length time segment based on an adjusted rule set corresponding to an adjusted time period, for updating the determination of whether the ECG rhythm is shockable or non-shockable.

30. The defibrillator of claim 21, wherein the comprising an output circuit that is configured to present a user interface configured for providing feedback indicating if the ECG rhythm is shockable or non-shockable.

31. The defibrillator of claim 21, wherein the defibrillator comprises an ambulatory medical device including a garment configured to:
  be worn about a torso of the patient for an extended period of time,
  support one or more components of the defibrillator, and
  receive at least one ECG sensing electrode for sensing the ECG signal of the patient and at least one therapy electrode for providing a therapeutic shock to the patient.

32. The defibrillator of claim 21, wherein analyzing the variable-length time segment of the ECG signal occurs approximately 0.5 seconds or less after identifying the chest compression interruption.

* * * * *

UNITED STATES PATENT AND TRADEMARK OFFICE
CERTIFICATE OF CORRECTION

PATENT NO.         : 10,155,120 B2
APPLICATION NO.    : 15/405377
DATED              : December 18, 2018
INVENTOR(S)        : Naveed Zaidi et al.

Page 1 of 1

It is certified that error appears in the above-identified patent and that said Letters Patent is hereby corrected as shown below:

<u>In Claim 30</u>
Column 46, Line 12, after "claim 21", delete "wherein the".

Signed and Sealed this
Nineteenth Day of February, 2019

Andrei Iancu
*Director of the United States Patent and Trademark Office*